US012359121B2

(12) United States Patent
Ge et al.

(10) Patent No.: US 12,359,121 B2
(45) Date of Patent: Jul. 15, 2025

(54) NEUTRAL FLUORESCENT MITOCHONDRIAL MARKER AS AMIDE DERIVATIVE, AND PREPARATION METHOD AND USE THEREOF

(71) Applicant: SOOCHOW UNIVERSITY, Suzhou (CN)

(72) Inventors: Jianfeng Ge, Suzhou (CN); Wei Ma, Suzhou (CN); Ru Sun, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 845 days.

(21) Appl. No.: 17/629,599

(22) PCT Filed: Feb. 4, 2021

(86) PCT No.: PCT/CN2021/075159
§ 371 (c)(1),
(2) Date: Jan. 24, 2022

(87) PCT Pub. No.: WO2022/147872
PCT Pub. Date: Jul. 14, 2022

(65) Prior Publication Data
US 2023/0159819 A1    May 25, 2023

(30) Foreign Application Priority Data

Jan. 5, 2021   (CN) .......................... 202110009534.0

(51) Int. Cl.
*C09K 11/06* (2006.01)
*G01N 33/58* (2006.01)

(52) U.S. Cl.
CPC ............ *C09K 11/06* (2013.01); *G01N 33/582* (2013.01); *C09K 2211/1033* (2013.01); *C09K 2211/1088* (2013.01)

(58) Field of Classification Search
CPC ............ C09K 11/06; C09K 2211/1033; C09K 2211/1088
See application file for complete search history.

(56) References Cited

U.S. PATENT DOCUMENTS

| | | | | | |
|---|---|---|---|---|---|
| 3,897,419 | A | * | 7/1975 | Bender ............... | C07D 311/16 544/58.7 |
| 6,379,823 | B1 | * | 4/2002 | Nii ..................... | C07D 241/46 313/506 |
| 12,157,271 | B2 | * | 12/2024 | Deininger ........... | B33Y 40/10 |
| 2004/0054174 | A1 | * | 3/2004 | Nakaya ............... | C09K 11/06 544/99 |
| 2005/0113575 | A1 | * | 5/2005 | Nakaya ............... | H05B 33/14 544/101 |
| 2013/0334461 | A1 | * | 12/2013 | Kubota ............... | C07D 265/36 568/717 |
| 2021/0115000 | A1 | * | 4/2021 | Korber ............... | C07D 265/38 |

FOREIGN PATENT DOCUMENTS

| | | | | | |
|---|---|---|---|---|---|
| CN | 1506359 | A | * | 6/2004 | ........... C07D 311/16 |
| CN | 108752327 | A | * | 11/2018 | ........... C07D 413/04 |
| EP | 0885263 | B1 | * | 4/2001 | ............. C09B 19/00 |
| FR | 2549832 | A1 | * | 2/1985 | ........... C07D 311/16 |
| GB | 2388595 | A | * | 11/2003 | ............. A01N 43/16 |
| JP | 2016138053 | A | | 8/2016 | |
| SU | 1109393 | A1 | * | 8/1984 | ........... C07D 265/34 |
| SU | 1505941 | A1 | * | 9/1989 | ........... C07D 311/16 |
| WO | 2016171755 | A1 | | 10/2016 | |
| WO | 2019104199 | A1 | | 5/2019 | |
| WO | WO-2019210190 | A2 | * | 10/2019 | ......... A61K 49/0028 |
| WO | WO-2022023353 | A1 | * | 2/2022 | ........... C07D 403/04 |

OTHER PUBLICATIONS

Akimov et al. "Luminescence spectr and lasing characteristics of some new coumarins", Soviet Journal of Quantum Electronics, 22(11), 999. Published Nov. 1992 (Year: 1992).*
Al-Kindy et al. "synthesis and spectroscopic study of 2,7-diethylamino-2-oxo-2H-chromen-3-yl benzothiazole-6-sulfonyl chlorides and its derivatives", Arabian Journal of Chemistry, 10, s117-s120, 2017. Published Aug. 4, 2012 (Year: 2012).*
Gordeeva et al. "Photochemical reactions of 7-aminocoumarins. 10* Reaction of 3-iodo-4-methyl-7-diethylaminocoumarin with heteroaromatic compounds", Chemistry Heterocyclic Compounds, vol. 26, p. 1222-1226, 1990. Published Nov. 1990 (Year: 1990).*
Griffiths et al. "the influence of chain length and electron acceptor residues in 3-substituted 7-N, N-diethylaminocoumarin dyes", vol. 28, No. 4, pp. 327-339, 1995. Published 1995 (available online Feb. 4, 2000). (Year: 1995).*
Kirpichenok et al. "reactions of 4-methyl-7-diethylaminocoumarin that proceed with electron transfer", Chemistry Heterocyclic Compounds, vol. 25, p. 737-745, 1989. Published Jul. 1989 (Year: 1989).*
Kirpichenok et al. "photochemical reactions of 7-aminocoumarins. 6* Reaction of 7-dialkylaminocoumarins with halo derivatives", Chemistry Heterocyclic Compounds, vol. 26, p. 858-862, 1990. Published Aug. 1990 (Year: 1990).*

(Continued)

*Primary Examiner* — Jane L Stanley
(74) *Attorney, Agent, or Firm* — SZDC Law PC

(57) ABSTRACT

The present invention relates to a series of neutral fluorescent mitochondrial markers as amide derivatives, and a preparation method and use thereof. The present invention provides for the first time that neutral dyes have excellent mitochondria targeting ability after being bonded to an amide compound. The present invention solves the problems of uncertain organelle targeting ability of the existing fluorescent dyes with a neutral structure and that the neutral dye is a commercial marker for lipid droplets in cells. In the present invention, the organelle targeting ability of a fluorescent dye is regulated by creatively modifying the structure, while the optical performance of the original dye is improved; and the biological properties of the dye are obviously improved after being bonded to an amide compound. Amide compounds are cheap and readily available, which is conducive to controlling the cost of new dyes, thus having great scientific significance and commercial value.

10 Claims, 14 Drawing Sheets

(56) References Cited

OTHER PUBLICATIONS

Kiripchenok et al. "photochemical reactions of 7-aminocoumarins. 4* reaction of 4-methyl-7-diethylaminocoumarin with compounds tending to photocatalytic dissociation", vol. 25, p. 380-388, 1989. Published Apr. 1989 (Year: 1989).*

Kitamura et al. "synthesis, absorption, and fluorescence properties and crystal structures of 7-aminocoumarin derivatives", Journal of Photochemistry and Photobiology A: Chemistry, 188, 2007, 378-386. Published online Jan. 4, 2007 (Year: 2007).*

Ma et al. Journal of Materials Chemistry B, 2021 (Year: 2021).*

Patalakha et al. "Luminescence-spectral and acid-base characteristics of 3-aryl-7-diethylaminocoumarins", Chemistry Heterocyclic Compounds, vol. 27, p. 32-37, 1991. Published Jan. 1991 (Year: 1991).*

Vina et al. "3-substituted coumarins as dual inhibitors of AChE and MAO for the treatment of Alzheimer's diesase", Medicinal Chemistry Communications, 2012, 3, 213-218. Published online Oct. 26, 2011 (Year: 2011).*

Wang et al. "the application of nitrogen heterocycles in mitochondrial-targeting fluorescent markers with neutral skeletons", Journal of Materials Chemistry B, 2020, 8, 7466-7474. Published online Jun. 29, 2020 (Year: 2020).*

Xu et al., "A coumarin-indole based colorimetric and "turn on" fluorescent probe for cyanide" Spectrochimica Acta Part A: Molecular and Biomolecular Spectroscopy 138 (2015) 164-168 (Nov. 22, 2014).

Takechi et al., "Synthesis of 4-(7-Diethylaminocoumarin-3-yl)benzeneisocyanate (DACB-NCO): A Highly Sensitive Fluorescent Derivatization Reagent for Alcohols in High-Performance Liquid Chromatography" J. Heterocyclic Chem., 38, 333-338 (Dec. 31, 2001).

Li, "Design of turn-on fluorescent probes and the application in detection of hydrogen sulfide and pH," Thesis for Master Degree, Liaoning University, Feb. 28, 2017.

* cited by examiner

NEUTRAL FLUORESCENT MITOCHONDRIAL MARKER AS AMIDE DERIVATIVE, AND PREPARATION METHOD AND USE THEREOF

This application is the National Stage Application of PCT/CN2021/075159, filed on Feb. 4, 2021, which claims priority to Chinese Patent Application No. 202110009534.0, filed on Jan. 5, 2021, which is incorporated by reference for all purposes as if fully set forth herein.

FIELD OF THE INVENTION

The present invention relates to fluorescent marker technology, and more particularly to a neutral fluorescent mitochondrial marker as an amide derivative, and a preparation method and use thereof.

DESCRIPTION OF THE RELATED ART

Mitochondria are dual-membrane organelles present in most cells, which are structures responsible for energy production and main sites where aerobic respiration occurs in cells. In addition to being the main sites for aerobic respiration and providing energy for cells, mitochondria also participate in important physiological activities such as genetic material transfer and cell differentiation, and have the ability to regulate cell growth and cell cycle. Therefore, in scientific research, real-time monitoring of mitochondria is particularly important. Among various technical means, fluorescent labeling technology becomes notable due to its simple operation and low preparation cost. Various fluorescent probes and dyes targeting mitochondria are developed accordingly.

In the past two decades, researchers have synthesized a variety of fluorescent mitochondrial probes, with which mitochondrial imaging is achieved by detecting metal ions (see Sreenath, K.; Allen, J. R.; Davidson, M. W.; Zhu, L. Chem. Commun. (Camb) 2011, 47, 11730), small organic molecules (see Ji, A.; Fan, Y.; Ren, W.; Zhang, S.; Ai, H. W. ACS Sens, 2018, 3, 992), and macromolecules (see Yang, L.; Niu, J.-Y.; Sun, R.; Xu, Y.-J.; Ge, J.-F. Sens Actuators B, 2018, 259, 299) in mitochondria. Given the reported fluorescent probes and dyes targeting mitochondria, it can be easily found that they mostly have a triphenylphosphonium, a pyridinium and an indolium in their main structures. This is true even for the most commonly used commercial red and green mitochondrial markers. This is because the presence of a proton pump on the inner mitochondrial membrane makes it easier for these cationic dyes to penetrate the mitochondrial membrane and accumulate in the mitochondria. However, they are accompanied by problems that these cations will change the mitochondrial membrane potential after entering the mitochondria, causing changes in the cell microenvironment and leading to cell apoptosis.

Therefore, there is an urgent need for a fluorescent dye with a neutral structure and having the ability to target mitochondria.

SUMMARY OF THE INVENTION

To solve the above technical problems, an object of the present invention is to provide a neutral fluorescent mitochondrial marker as an amide derivative and a preparation method and use thereof. The present invention provides an amide derivative having excellent mitochondria targeting ability. The neutral dye targets mitochondria independent of the negative charge on the inner mitochondrial membrane, thus solving the defects of the existing cationic mitochondrial dyes.

A first object of the present invention is to provide a neutral fluorescent mitochondrial marker as an amide derivative, represented by one of Formulas (I)-(IV):

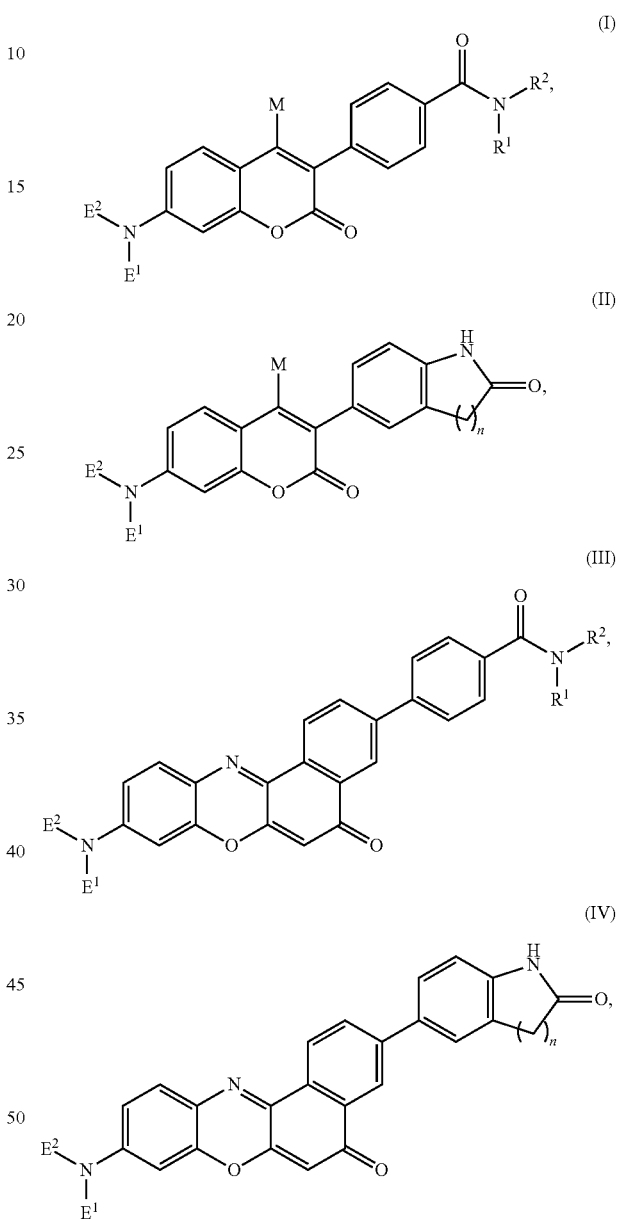

where $R^1$ and $R^2$ are each independently selected from hydrogen or an alkyl group having 1 to 6 carbon atoms; M, $E^1$, and $E^2$ are each independently selected from an alkyl group having 1 to 6 carbon atoms; and n is any integer from 1 to 3.

The alkyl group in the present invention means a saturated branched or straight monovalent hydrocarbon group with 1 to 6 carbon atoms, such as methyl (Me), n-butyl (Bu), ethyl (Et) and the like.

Further, $R^1$ and $R^2$ are each independently selected from hydrogen or methyl; M is methyl; $E^1$ and $E^2$ are both ethyl; and n is 1 or 2.

The compounds of Formula (I)-(IV) all include a fluorescent dye and an amide compound connected thereto through a chemical bond. In the present invention, a coumarin borate derivative and a Nile red borate derivative targeting lipid droplets are bonded to an amide compound to successfully impart them the mitochondria targeting ability. In the present invention, the organelle targeting ability of a fluorescent dye is regulated by modifying the structure, while the optical performance of original dye is improved. Moreover, the biological performance of the dye is significantly improved after being bond to the amide compound. Amide compounds are cheap and readily available, which is conducive to controlling the cost of new dyes, thus having great scientific significance and commercial value.

A second object of the present invention is to provide a method for preparing the neutral fluorescent mitochondrial marker as an amide derivative, which includes the following steps:

reacting a compound of Formula (2) with a compound of Formulas (1a-c) or Formulas (1d-e) in an organic solvent under a weakly basic condition, to obtain a neutral fluorescent mitochondrial marker as an amide derivative of Formula (I) or Formula (II); or reacting a compound of Formula (3) with a compound of Formulas (1a-c) or Formulas (1d-e) in an organic solvent under a weakly basic condition, to obtain a neutral fluorescent mitochondrial marker as an amide derivative of Formula (III) or Formula (IV).

The structural formulas of Formulas (1a-c), (1d-e), (2) and (3) are shown below:

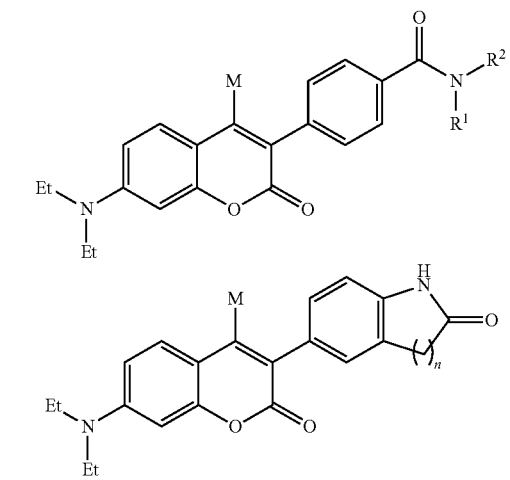

where $R^1$ and $R^2$ are each independently selected from hydrogen or an alkyl group having 1 to 6 carbon atoms; M, $E^1$, and $E^2$ are each independently selected from an alkyl group having 1 to 6 carbon atoms; and n is any integer from 1 to 3.

Preferably, $R^1$ and $R^2$ are each independently selected from hydrogen or methyl; M is methyl; $E^1$ and $E^2$ are both ethyl; and n is 1 or 2. Particularly, the neutral fluorescent mitochondrial marker as an amide derivative has a structure below:

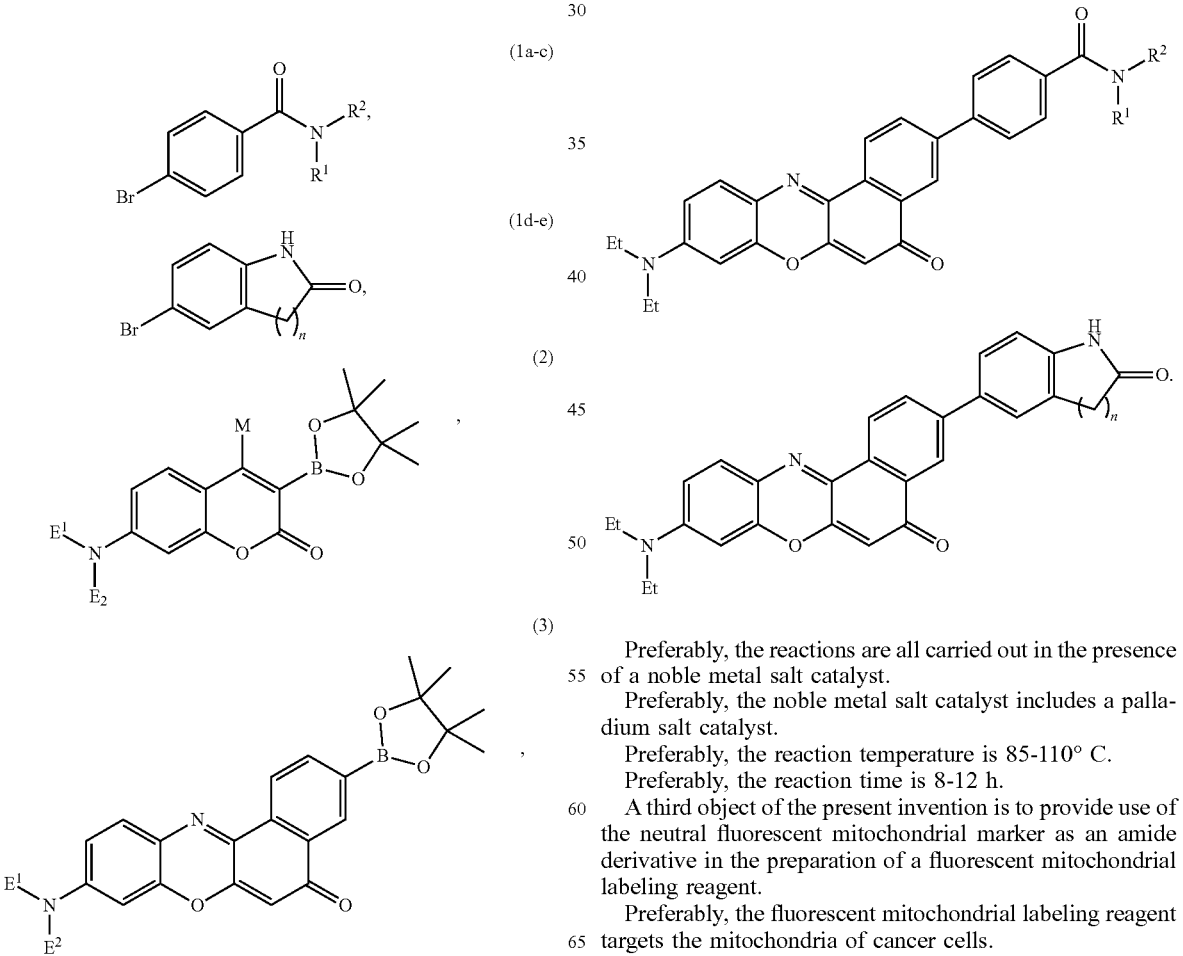

Preferably, the reactions are all carried out in the presence of a noble metal salt catalyst.

Preferably, the noble metal salt catalyst includes a palladium salt catalyst.

Preferably, the reaction temperature is 85-110° C.

Preferably, the reaction time is 8-12 h.

A third object of the present invention is to provide use of the neutral fluorescent mitochondrial marker as an amide derivative in the preparation of a fluorescent mitochondrial labeling reagent.

Preferably, the fluorescent mitochondrial labeling reagent targets the mitochondria of cancer cells.

Preferably, a method for cell imaging using a fluorescent mitochondrial labeling reagent includes the following steps:

co-incubating the fluorescent mitochondrial labeling reagent and cells for 10 min or more at 37° C. and 5% $CO_2$, then imaging the cells under a laser confocal microscope, and collecting a fluorescent signal.

Preferably, when the fluorescent mitochondrial labeling reagent includes the neutral fluorescent mitochondrial marker as an amide derivative of Formula (I) or Formula (II), the reagent is excited using a blue light channel, specifically a 405 nm light source, and a fluorescent signal in the range of 410 to 500 nm is collected. The neutral fluorescent mitochondrial marker as an amide derivative of Formula (I) or Formula (II) is a blue mitochondrial marker.

When the fluorescent mitochondrial labeling reagent includes the neutral fluorescent mitochondrial marker as an amide derivative of Formula (III) or Formula (IV), the reagent is excited using a red light channel, specifically a 561 nm light source, and a fluorescent signal in the range of 570 to 750 nm is collected. The neutral fluorescent mitochondrial marker as an amide derivative of Formula (III) or Formula (IV) is a red mitochondrial marker.

By means of the above technical solutions, the present invention has the following advantages.

The present invention provides a neutral fluorescent mitochondrial marker as an amide derivative for the first time, which regulates the organelle targeting ability of an original fluorophore by creative modification of its structure while the optical performance of the fluorophore is kept unchanged. Moreover, the biological properties of the dye are significantly improved after the dye is bonded to the amide compound. The amide compound is cheap and readily available, which is beneficial to the control of the cost of the new dye. Due to the electrically neutral structure, such compounds can target the mitochondria without changing the membrane potential of the mitochondria, and have good biological compatibility and low cytotoxicity.

After the neutral fluorescent mitochondrial marker as an amide derivative of the present invention is co-incubated with cells, imaging of mitochondria in the cells can be realized. When used for cell imaging, the compounds of the present invention have low cytotoxicity and little damage to biological samples, are not affected by other organelles, and enable the observation of a cell sample for a long time, thus having great scientific significance and commercial value. The present invention solves the problems of uncertain organelle targeting ability of the existing fluorescent dyes with a neutral structure and that the neutral dye is a commercial marker for lipid droplets in cells.

The above description is only a summary of the technical solutions of the present invention. To make the technical means of the present invention clearer and implementable in accordance with the disclosure of the specification, the preferred embodiments of the present invention will be described in detail with reference to the accompanying drawings.

BRIEF DESCRIPTION OF THE DRAWINGS

FIG. 27 shows the test results of the anti-photobleaching performance of dye 2a;
and
FIG. 28 shows the test results of the anti-photobleaching performance of dye 3a.

DETAILED DESCRIPTION OF THE PREFERRED EMBODIMENTS

The specific embodiments of the present invention will be described in further detail with reference to embodiments. The following embodiments are intended to illustrate the present invention, instead of limiting the scope of the present invention.

In the following examples, the cells are imaged under a laser confocal microscope; in the blue channel, light of 405 nm is used for excitation, and a fluorescence signal in the range of 410-500 nm is collected; in the green channel, light of 488 nm is used for excitation, and a fluorescence signal in the range of 500-550 nm is collected; and in the red channel, light of 561 nm is used for excitation, and a fluorescence signal in the range of 570-750 nm is collected.

Figure 1:
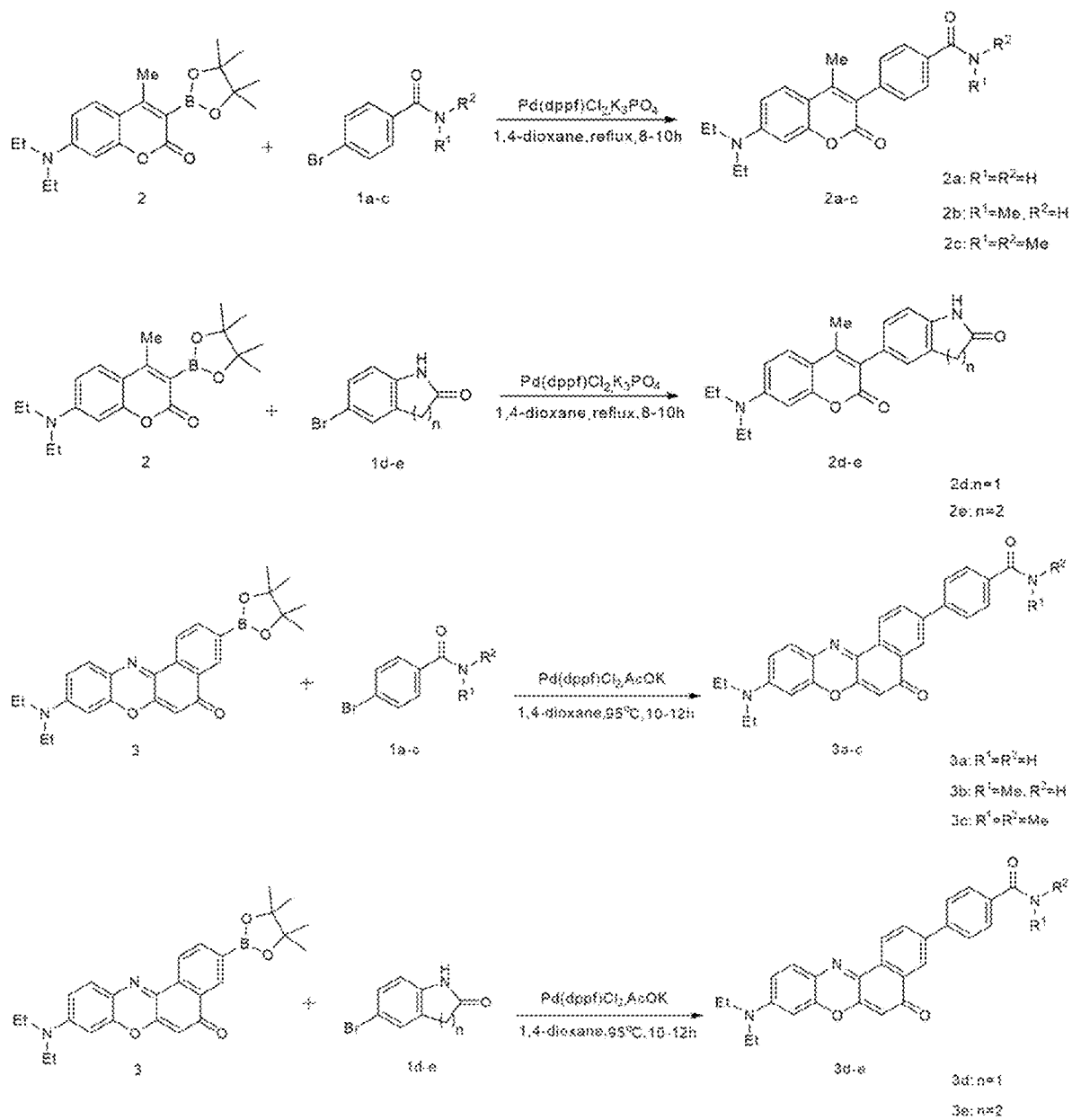
FIG. 1 is a schematic diagram showing a synthesis route of a dye according to the present invention.

The synthesis route in the examples of the present invention is shown in FIG. 1, where the number below the chemical formula represents the compound. In the synthesis of the compound of the present invention, the ratios of raw materials and the purification methods are conventional ratios or conventional purification methods.

The examples are illustrative, and the product structure is confirmed by nuclear magnetic resonance in the present invention.

Example 1

General Steps for the Synthesis of Dyes 2a-e:

Compound 2 (1.0 mmol, 357.2 mg), one of the amide compounds 1a-e (1.0 mmol), [1,1'-bis(diphenylphosphino) ferrocene]palladium dichloride (Pd(dppf)Cl$_2$, 0.03 mmol, 22 mg), and potassium phosphate (K$_3$PO$_4$, 2.5 mmol, 557.5 mg) were dissolved in 1,4-dioxane (15.0 ml) as a solvent.

Then the reaction system was purged three times with nitrogen and then refluxed for 8 to 10 hrs. The progress of the reaction was monitored by TLC. After cooling to room temperature, the reaction mixture was suction filtered, and the filtrate was rotary evaporated to remove the solvent. The residue was separated by column chromatography (eluant: dichloromethane/methanol (100/1, v/v)) to obtain the dyes 2a-e.

Particularly, the specific raw materials for the synthesis and the yield of each product, and the structural characterization results were as follows:

The dye 2a (262.0 mg) was prepared with Compound 2 (1 mmol, 357.21 mg) and Compound 1a (1 mmol, 200.0 mg), which was a yellow solid and had a yield of 75.0%. Characterization of dye 2a: mp 195.4-200.5° C. IR ν (KBr, cm$^{-1}$): 3404, 3128, 2974, 2928, 2868, 1672, 1605, 1575, 1163, 1305, 1092, 856, 802, 770, 658. $^1$H NMR (400 MHz, CDCl$_3$): δ (ppm) 7.87 (d, J=7.9 Hz, 2H, 2×Ar—H), 7.47 (d, J=8.9 Hz, 1H, Ar—H), 7.40 (d, J=7.8 Hz, 2H, 2×Ar—H), 6.64 (d, J=10.2 Hz, 1H, Ar—H), 6.55 (s, 1H, Ar—H), 6.23 (s, 1H, N—H), 5.72 (s, 1H, N—H), 3.44 (q, J=7.0 Hz 4H, 2×CH$_2$), 2.23 (s, 3H, CH$_3$), 1.23 (t, J=6.8 Hz, 6H, 2×CH$_3$). $^{13}$C NMR (151 MHz, DMSO-d$_6$): δ (ppm) 167.5, 160.3, 154.6, 150.1, 148.6, 138.2, 133.1, 130.3, 127.0, 126.7, 118.9, 108.7, 108.3, 96.4, 43.9, 16.0, 12.2. HRMS (ESI$^+$): m/z calcd C$_{21}$H$_{23}$N$_2$O$_3^+$ for [M+H]$^+$ 351.1703. found: 351.1741.

The dye 2b (262.1 mg) was prepared with Compound 2 (1 mmol, 357.21 mg) and Compound 1b (1 mmol, 214.1 mg), which was a pale yellow solid and had a yield of 72.1%. Characterization of dye 2b: mp 180.5-185.0° C. IR ν (KBr, cm$^{-1}$): 3299, 3055, 2976, 2936, 1711, 1620, 1609, 1523, 1406, 1316, 1213, 1165, 935, 793, 669. $^1$H NMR (400 MHz, CDCl$_3$): δ (ppm) 7.80 (d, J=7.9 Hz, 2H, 2×Ar—H), 7.46 (d, J=8.9 Hz, 1H, Ar—H), 7.36 (d, J=7.9 Hz, 2H, 2×Ar—H), 6.63 (d, J=10.2 Hz, 1H, Ar—H), 6.55 (s, 1H, Ar—H), 6.29 (s, 1H, N—H), 3.44 (q, J=7.1 Hz, 4H, 2×CH$_2$), 3.02 (d, J=4.63 Hz, 3H, CH$_3$), 2.23 (s, 3H, CH$_3$), 1.23 (t, J=6.8 Hz, 6H, 2×CH$_3$). $^{13}$C NMR (151 MHz, CDCl$_3$): δ (ppm) 168.1, 161.8, 155.1, 150.4, 148.9, 138.5, 133.8, 130.8, 126.8, 126.2, 120.0, 109.3, 108.7, 97.4, 44.7, 26.8, 16.3, 12.4. HRMS (ESI$^+$): m/z calcd C$_{22}$H$_{25}$N$_2$O$_3$+ for [M+H]$^+$ 365.1860. found: 365.1992.

The dye 2c (302.6 mg) was prepared with Compound 2 (1 mmol, 357.21 mg) and Compound 1c (1 mmol, 228.0 mg), which was a yellow solid and had a yield of 80.0%. Characterization of dye 2c: mp 175.5-180.0° C. IR ν (KBr, cm$^{-1}$): 2971, 2928, 1702, 1628, 1617, 1508, 1442, 1357, 1213, 1164, 1080, 983, 918, 876, 782, 679, 632. $^1$H NMR (400 MHz, CDCl$_3$): δ (ppm) 7.49 (d, J=7.5 Hz, 2H, 2×Ar—H), 7.46 (d, J=9.1 Hz, 1H, Ar—H), 7.35 (d, J=7.4 Hz, 2H, 2×Ar—H), 6.63 (d, J=8.9 Hz, 1H, Ar—H), 6.56 (s, 1H, Ar—H), 3.43 (q, J=7.0 Hz, 4H, 2×CH$_2$), 3.14 (s, 3H, CH$_3$), 3.05 (s, 3H, CH$_3$), 2.23 (s, 3H, CH$_3$), 1.23 (t, J=6.7 Hz, 6H, 2×CH$_3$). $^{13}$C NMR (151 MHz, CDCl$_3$): δ (ppm) 171.5, 161.8, 155.1, 150.4, 148.9, 136.8, 135.4, 130.6, 127.0, 126.1, 120.1, 109.3, 108.7, 97.4, 44.7, 39.7, 35.4, 16.3, 12.4. HRMS (ESI$^+$): m/z calcd C$_{23}$H$_{27}$N$_2$O$_3^+$ for [M+H]$^+$ 379.2016. found: 379.2020.

The dye 2d (307.7 mg) was prepared with Compound 2 (1 mmol, 357.21 mg) and Compound 1d (1 mmol, 212.0 mg), which was a yellow solid and had a yield of 85.0%. Characterization of dye 2d: mp 168.5-173.0° C. IR ν (KBr, cm$^{-1}$): 3143, 2975, 2916, 1701, 1584, 1522, 1409, 1354, 1263, 1211, 1162, 990, 867, 798, 689. $^1$H NMR (400 MHz, CDCl$_3$): δ (ppm) 8.39 (s, 1H, N—H), 7.46 (d, J=8.9 Hz, 1H, Ar—H), 7.18 (s, 1H, Ar—H), 7.13 (d, J=7.8 Hz, 1H, Ar—H), 6.93 (d, J=7.1 Hz, 1H, Ar—H), 6.63 (d, J=7.8 Hz, 1H, Ar—H), 6.55 (s, 1H, Ar—H), 3.59 (s, 2H, CH$_2$), 3.44 (q, J=7.1 Hz, 4H, 2×CH$_2$), 2.25 (s, 3H, CH$_3$), 1.22 (t, J=6.8 Hz, 6H, 2×CH$_3$). $^{13}$C NMR (151 MHz, CDCl$_3$): δ (ppm) 177.4, 162.3, 154.9, 150.1, 148.4, 141.8, 130.1, 129.3, 126.7, 126.0, 125.2, 120.5, 109.4, 109.3, 108.5, 97.3, 44.6, 36.1, 16.2, 12.3. HRMS (ESI$^+$): m/z calcd C$_{22}$H$_{23}$N$_2$O$_3^+$ for [M+H]$^+$ 363.1703. found: 363.1700.

The dye 2e (308.3 mg) was prepared with Compound 2 (1 mmol, 357.21 mg) and Compound 1e (1 mmol, 226.0 mg), which was a yellow solid and had a yield of 82.0%. Characterization of dye 2e: mp 173.5-178.0° C. IR ν (KBr, cm$^{-1}$): 3177, 3041, 2967, 1703, 1674, 1618, 1545, 1443, 1356, 1282, 1183, 1145, 1006, 949, 904, 865, 738, 697. $^1$H NMR (400 MHz, CDCl$_3$): δ (ppm) 8.79 (s, 1H, N—H), 7.46 (d, J=8.9 Hz, 1H, Ar—H), 7.13 (s, 1H, Ar—H), 7.09 (d, J=8.0 Hz, 1H, Ar—H), 6.87 (d, J=7.8 Hz, 1H, Ar—H), 6.63 (d, J=7.8 Hz, 1H, Ar—H), 6.55 (s, 1H, Ar—H), 3.42 (q, J=7.1 Hz, 4H, 2×CH$_2$), 2.99 (t, J=7.1 Hz, 2H, CH$_2$), 2.68 (t, J=7.2, 2H, CH$_2$), 2.25 (s, 3H, CH$_3$), 1.22 (t, J=6.8 Hz, 6H, 2×CH$_3$). $^{13}$C NMR (151 MHz, CDCl$_3$): δ (ppm) 171.6, 162.2, 155.0, 150.2, 148.4, 136.6, 130.1, 129.7, 126.7, 126.0, 123.5, 120.3, 115.1, 109.4, 108.6, 97.4, 44.7, 30.6, 25.4, 16.3, 12.4. HRMS (ESI$^+$): m/z calcd C$_{23}$H$_{25}$N$_2$O$_3^+$ for [M+H]$^+$ 377.1860. found: 377.1967.

Example 2

General Steps for the Synthesis of Dyes 3a-e:

Compound 3 (0.5 mmol, 222.1 mg), one of the amide compound 1a-e (0.6 mmol), [1,1'-bis(diphenylphosphino)ferrocene]palladium dichloride (Pd(dppf)Cl$_2$, 0.015 mmol, 12 mg), and potassium acetate (AcOK, 1.5 mmol, 334.5 mg) were dissolved in 1,4-dioxane (15.0 ml) as a solvent. Then the reaction system was purged three times with nitrogen and heated for 10 to 12 hrs at 95° C. The progress of the reaction was monitored by TLC. After cooling to room temperature, the reaction mixture was suction filtered, and the filtrate was rotary evaporated to remove the solvent. The residue was separated by column chromatography (eluant: dichloromethane/methanol (50/1, v/v)) to obtain pure dyes.

Particularly, the specific raw materials for the synthesis and the yield of each product, and the structural characterization results were as follows:

The dye 3a (65.5 mg) was prepared with Compound 3 (0.5 mmol, 222.1 mg) and Compound 1a (0.6 mmol, 120.0 mg), which was a dark green solid and had a yield of 30.0%. Characterization of dye 3a: mp 212.5-215.0° C. IR ν (KBr, cm$^{-1}$): 3327, 3144, 2965, 2923, 1701, 1682, 1636, 1619, 1520, 1409, 1323, 1230, 1147, 1009, 946, 845, 774, 669, 644. $^1$H NMR (400 MHz, DMSO-d$_6$): δ (ppm) 8.61 (d, J=8.3 Hz, 1H, Ar—H), 8.38 (s, 1H, Ar—H), 8.16 (d, J=8.9 Hz, 1H, Ar—H), 8.06 (s, 1H, Ar—H), 8.0 (d, J=8.1 Hz, 2H, 2×Ar—H), 7.88 (d, J=7.9 Hz, 2H, 2×Ar—H), 7.63 (d, J=8.9 Hz, 1H, Ar—H), 7.41 (s, 1H, Ar—H), 6.85 (d, J=7.4 Hz, 1H, Ar—H), 6.67 (s, 1H, N—H), 6.32 (s, 1H, N—H), 3.48 (q, J=7.0 Hz, 4H, 2×CH$_2$), 1.14 (t, J=6.8 Hz, 6H, 2×CH$_3$). $^{13}$C NMR (151 MHz, DMSO-d$_6$): δ (ppm) 181.7, 166.7, 159.5 151.2, 149.9, 145.8, 138.6, 133.3, 132.8, 131.1, 130.2, 129.4, 125.6, 124.8, 123.9, 123.2, 109.8, 109.7, 104.4, 95.9, 44.2, 12.3. HRMS (ESI$^+$): m/z calcd C$_{27}$H$_{24}$N$_3$O$_3^+$ for [M+H]$^+$ 438.1812. found: 438.1825.

The dye 3b (85.7 mg) was prepared with Compound 3 (0.5 mmol, 222.1 mg) and Compound 1b (0.6 mmol, 128.0 mg), which was a black solid and had a yield of 38.0%. Characterization of dye 3b: mp 198.5-203.0° C. IR ν (KBr, cm$^{-1}$): 3295, 2970, 1639, 1578, 1563, 1548, 1463, 1372, 1278, 1181, 1076, 950, 866, 768, 689. $^1$H NMR (400 MHz, DMSO-d$_6$): δ (ppm) 8.70 (d, J=8.3 Hz, 1H, Ar—H), 8.59 (s, 1H, Ar—H), 7.96 (d, J=8.3 Hz, 1H, Ar—H), 7.88 (d, 2H, J=7.6 Hz, 2×Ar—H), 7.82 (d, J=8.0 Hz, 2H, 2×Ar—H), 7.65 (d, J=8.9 Hz, 1H, Ar—H), 6.73 (d, J=8.9 Hz, 1H, Ar—H), 6.53 (s, 1H, Ar—H), 6.21 (s, 1H, N—H), 5.47 (d, J=8.9 Hz, 1H, Ar—H), 3.52 (q, J=7.0 Hz, 4H, 2×CH$_2$), 3.05 (d, J=3.7 Hz, CH$_3$), 1.28 (t, J=6.8 Hz, 6H, 2×CH$_3$). $^{13}$C NMR (151 MHz, TFA-d): δ (ppm) 170.5, 150.7, 148.9 143.0, 140.1, 135.7, 134.6, 132.2, 130.5, 130.4, 127.8, 127.6, 125.6, 124.5, 122.5, 119.2, 117.4, 115.5, 113.6, 111.7, 100.1, 97.3, 47.8, 29.7, 27.5, 12.4. HRMS (ESI$^+$): m/z calcd C$_{28}$H$_{26}$N$_3$O$_3$$^+$ for [M+H]$^+$ 452.1969. found: 452.2001.

The dye 3c (151.1 mg) was prepared with Compound 3 (0.5 mmol, 222.1 mg) and Compound 1c (0.6 mmol, 130.8 mg), which was a black solid and had a yield of 65.0%. Characterization of dye 3c: mp 200.0-205.5° C. IR ν (KBr, cm$^{-1}$): 2965, 2925, 1623, 1579, 1518, 1406, 1324, 1280, 1146, 1078, 1000, 950, 875, 799, 726, 680, 634. $^1$H NMR (400 MHz, CDCl$_3$): δ (ppm) 8.70 (d, J=8.3 Hz, 1H, Ar—H), 8.55 (s, 1H, Ar—H), 7.95 (d, J=8.2 Hz, 1H, Ar—H), 7.80 (d, J=7.4 Hz, 2H, 2×Ar—H), 7.61 (d, J=8.9 Hz, 1H, Ar—H), 7.55 (d, J=7.8 Hz, 2H, 2×Ar—H), 6.67 (d, J=8.7 Hz, 1H, Ar—H), 6.46 (s, 1H, Ar—H), 6.41 (s, 1H, Ar—H), 3.45 (q, J=7.1 Hz, 4H, 2×CH$_2$), 3.15 (s, 3H, CH$_3$), 3.05 (s, 3H, CH$_3$), 1.26 (t, J=6.9 Hz, 6H, 2×CH$_3$). $^{13}$C NMR (151 MHz, DMSO-d$_6$): δ (ppm) 183.4, 171.3, 152.2, 150.8, 146.7, 141.3, 141.1, 139.3, 135.6, 132.0, 131.1, 129.6, 127.8, 127.1, 125.1, 124.5, 123.9, 109.8, 105.7, 96.2, 45.1, 39.6, 35.4, 12.6. HRMS (ESI$^+$): m/z calcd C$_{29}$H$_{28}$N$_3$O$_3$$^+$ for [M+H]$^+$ 466.2125. found: 466.2123.

The dye 3d (75.3 mg) was prepared with Compound 3 (0.5 mmol, 222.1 mg) and Compound 1d (0.6 mmol, 127.2 mg), which was a black solid and had a yield of 32.0%. Characterization of dye 3d: mp 220.5-225.0° C. IR ν (KBr, cm$^{-1}$): 3252, 2971, 1713, 1641, 1619, 1520, 1467, 1375, 1353, 1271, 1177, 1094, 999, 887, 842, 828, 804, 719, 692, 674, 647, 636. $^1$H NMR (400 MHz, DMSO-d$_6$): δ (ppm) 10.52 (s, 1H, N—H), 8.56 (d, J=7.9 Hz, 1H, Ar—H), 8.28 (s, 1H, Ar—H), 8.05 (d, J=8.7 Hz, 1H, Ar—H), 7.66 (s, 1H, Ar—H), 7.62 (d, J=8.4 Hz, 2H, 2×Ar—H), 6.93 (d, J=7.9 Hz, 1H, Ar—H), 6.83 (d, J=7.8 Hz, 1H, Ar—H), 6.66 (s, 1H, Ar—H), 6.30 (s, 1H, Ar—H), 3.55 (s, 2H, CH$_2$), 3.47 (q, J=7.0 Hz, 4H, 2×CH$_2$), 1.13 (t, J=6.8 Hz, 6H, 2×CH$_3$). $^{13}$C NMR (151 MHz, TFA-d): δ (ppm) 180.2, 171.5, 150.8, 143.5, 141.1, 135.9, 135.7, 133.9, 131.4, 129.8, 128.0, 126.0, 125.3, 123.7, 123.0, 119.6, 115.3, 114.7, 113.5, 112.8, 112.0, 50.6, 10.8. HRMS (ESI$^+$): m/z calcd C$_{28}$H$_{24}$N$_3$O$_3$$^+$ for [M+H]$^+$ 450.1812. found: 450.1833.

The dye 3e (97.2 mg) was prepared with Compound 3 (0.5 mmol, 222.1 mg) and Compound 1e (0.6 mmol, 135.6 mg), which was a black solid and had a yield of 42.0%. Characterization of dye 3e: mp 230.0-235.0° C. IR ν (KBr, cm$^{-1}$): 3463, 3213, 2974, 1656, 1639, 1620, 1575, 1488, 1399, 1354, 1275, 1178, 1077, 998, 949, 847, 806, 739, 669, 649. $^1$H NMR (400 MHz, DMSO-d$_6$): δ (ppm) 10.25 (s, 1H, N—H), 8.59 (d, J=8.7 Hz, 1H, Ar—H), 8.34 (s, 1H, Ar—H), 8.10 (d, J=8.1 Hz, 1H, Ar—H), 7.66 (s, 1H, Ar—H), 7.62 (d, J=8.2 Hz, 2H, 2×Ar—H), 7.00 (d, J=7.9 Hz, 1H, Ar—H), 6.86 (d, J=7.0 Hz, 1H, Ar—H), 6.70 (s, 1H, Ar—H), 6.34 (s, 1H, Ar—H), 3.52 (q, J=7.0 Hz, 4H, 2×CH$_2$), 3.00 (t, J=6.9 Hz, 2H, CH$_2$), 1.23 (t, J=7.1 Hz, 2H, CH$_2$), 1.17 (t, J=6.9 Hz, 6H, 2×CH$_3$). $^{13}$C NMR (151 MHz, TFA-d): δ (ppm) 177.0, 150.7, 147.6, 142.9, 136.8, 135.7, 134.53, 133.8, 131.2, 129.8, 127.1, 127.0, 125.2, 124.5, 122.9, 119.6, 117.4, 115.4, 114.7, 113.5, 112.8, 102.2, 50.5, 28.9, 23.7, 10.8. HRMS (ESI$^+$): m/z calcd C$_{29}$H$_{26}$N$_3$O$_3$$^+$ for [M+H]$^+$ 464.1969. found: 464.1920.

Example 3

Figure 2:
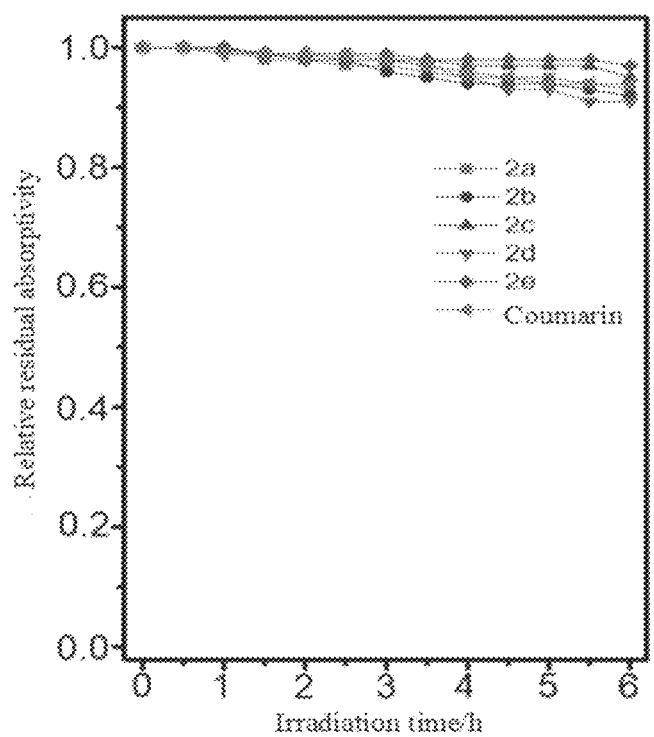
FIG. 2 shows the photostability test results of dyes 2a-e.
Figure 3:
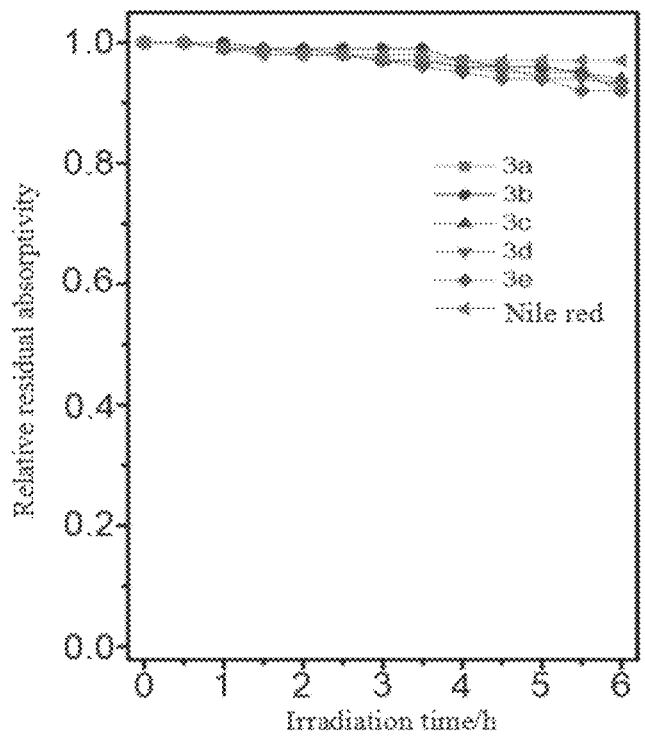
FIG. 3 shows the photostability test results of dyes 3a-e.
Figure 4:
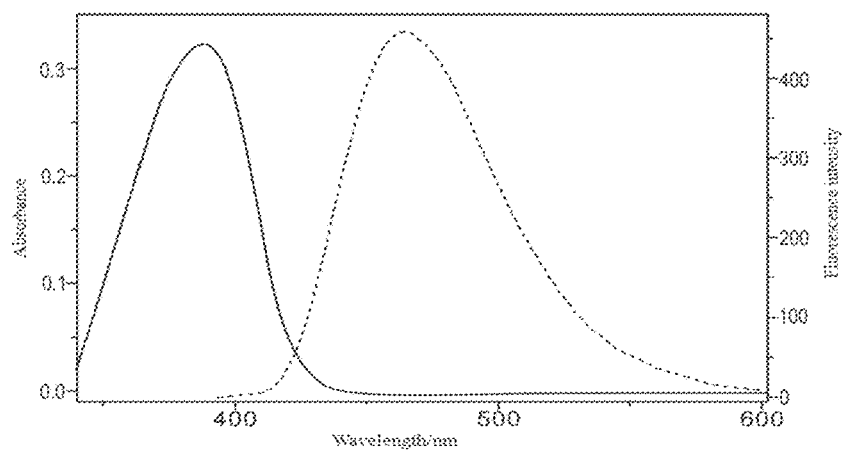
FIG. 4 shows the ultraviolet-visible absorption spectrum and fluorescence spectrum of dye 2a in chloroform.
Figure 5:
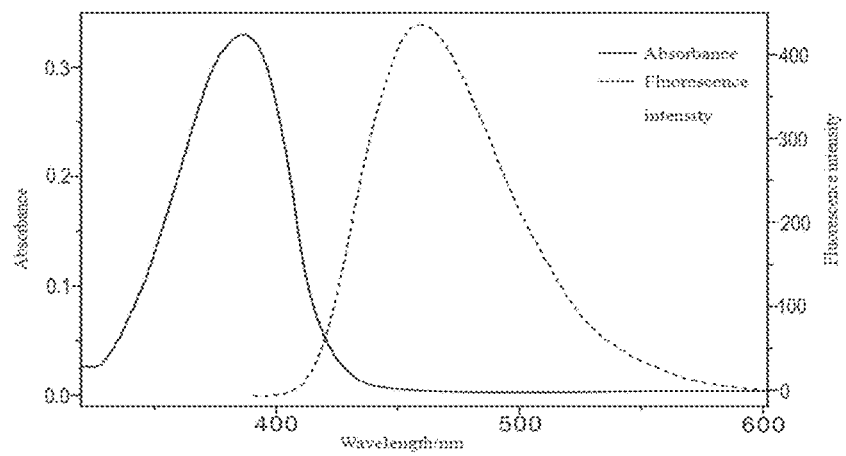
FIG. 5 shows the ultraviolet-visible absorption spectrum and fluorescence spectrum of dye 2b in chloroform.
Figure 6:
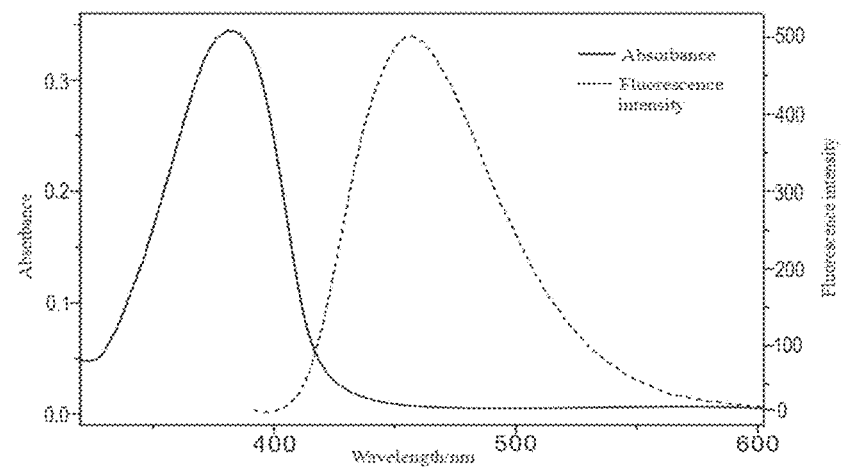
FIG. 6 shows the ultraviolet-visible absorption spectrum and fluorescence spectrum of dye 2c in chloroform.
Figure 7:
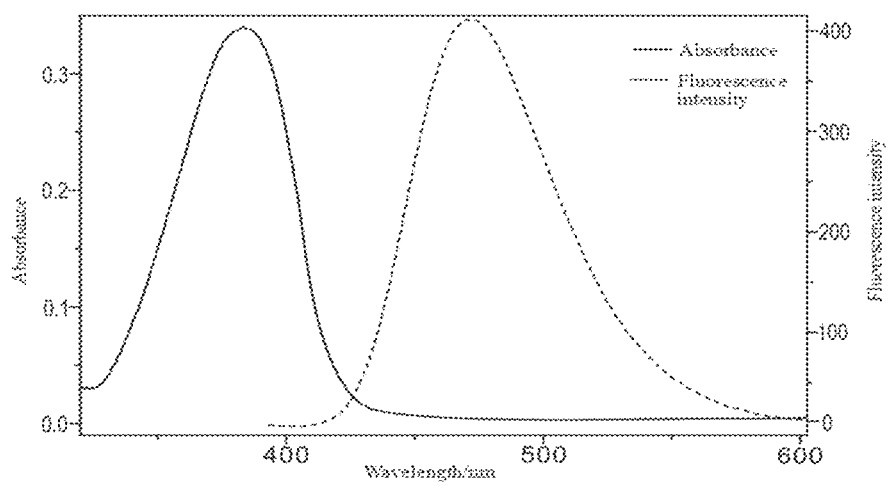
FIG. 7 shows the ultraviolet-visible absorption spectrum and fluorescence spectrum of dye 2d in chloroform.
Figure 8:
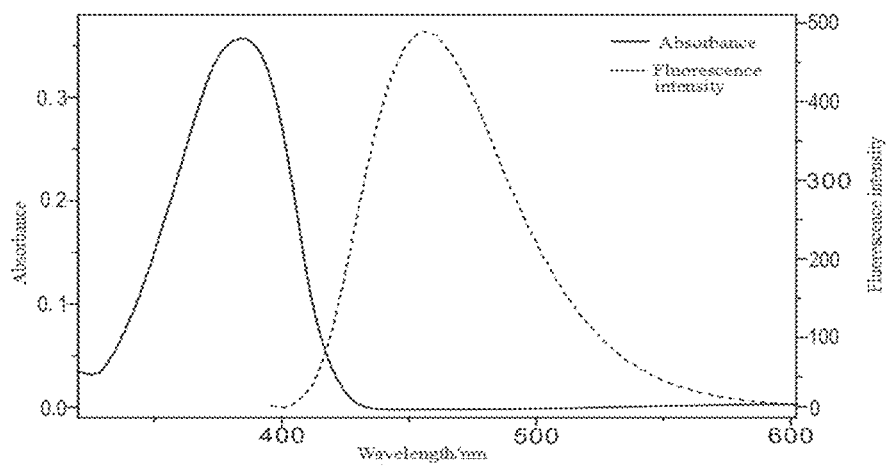
FIG. 8 shows the ultraviolet-visible absorption spectrum and fluorescence spectrum of dye 2e in chloroform.
Figure 9:
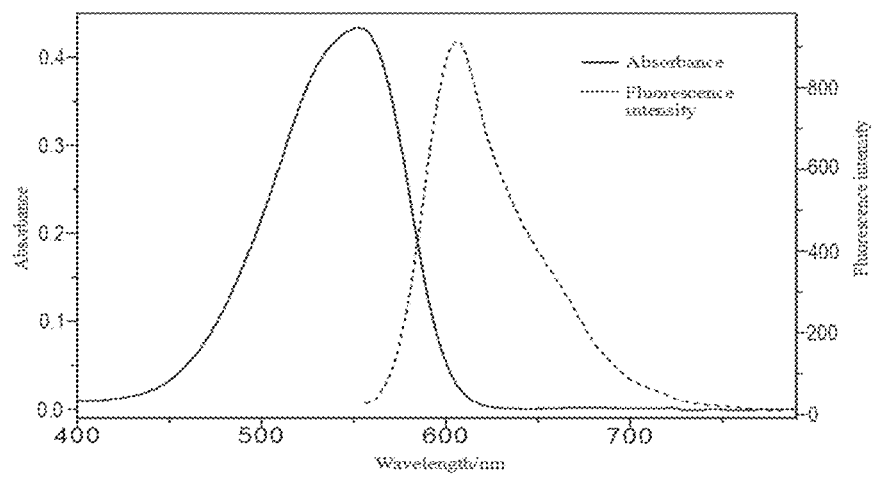
FIG. 9 shows the ultraviolet-visible absorption spectrum and fluorescence spectrum of dye 3a in chloroform.
Figure 10:
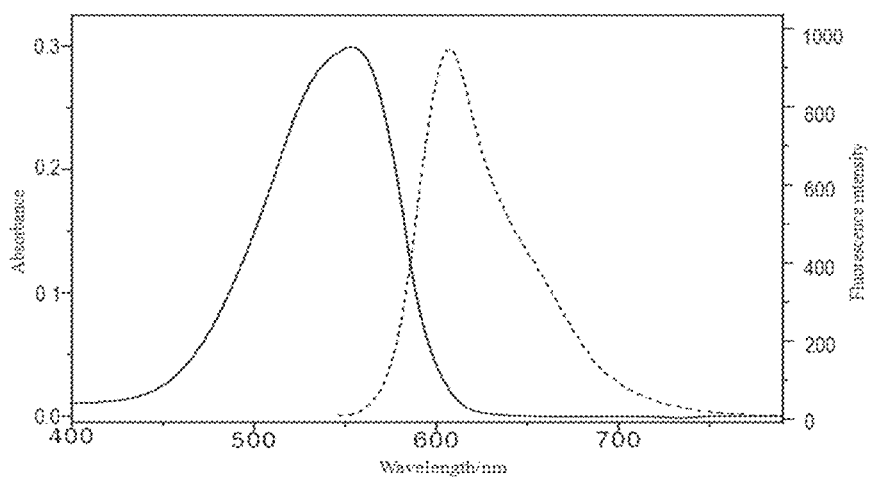
FIG. 10 shows the ultraviolet-visible absorption spectrum and fluorescence spectrum of dye 3b in chloroform.
Figure 11:
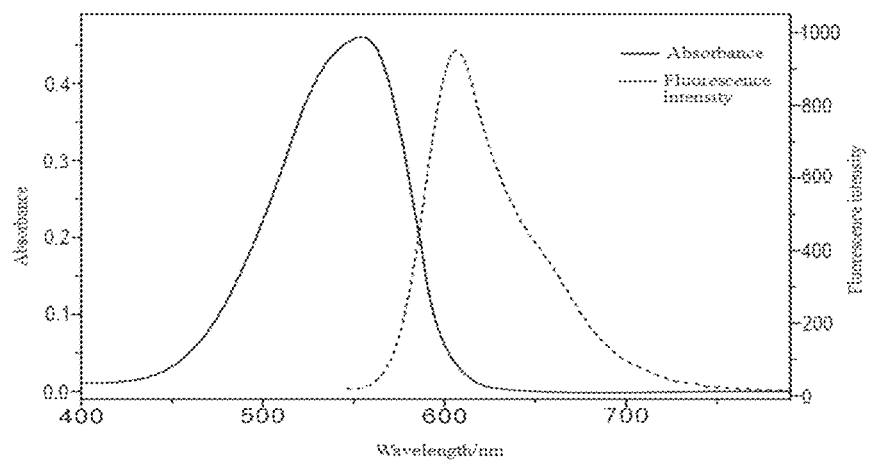
FIG. 11 shows the ultraviolet-visible absorption spectrum and fluorescence spectrum of dye 3c in chloroform.
Figure 12:
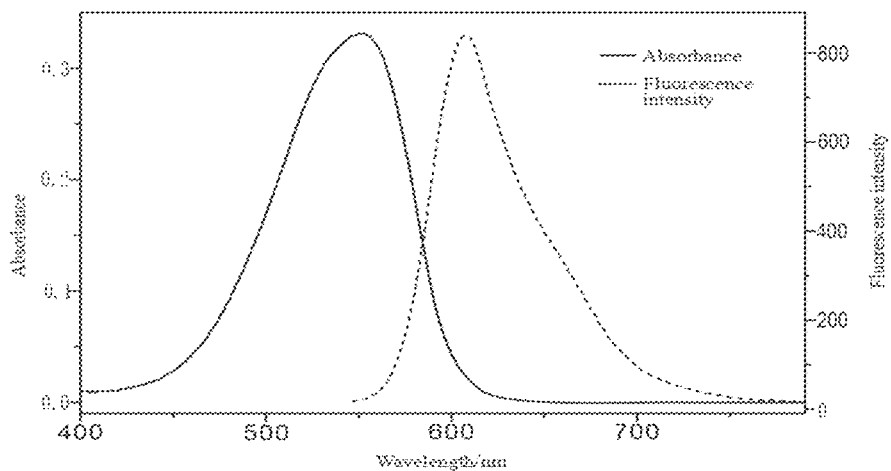
FIG. 12 shows the ultraviolet-visible absorption spectrum and fluorescence spectrum of dye 3d in chloroform.
Figure 13:
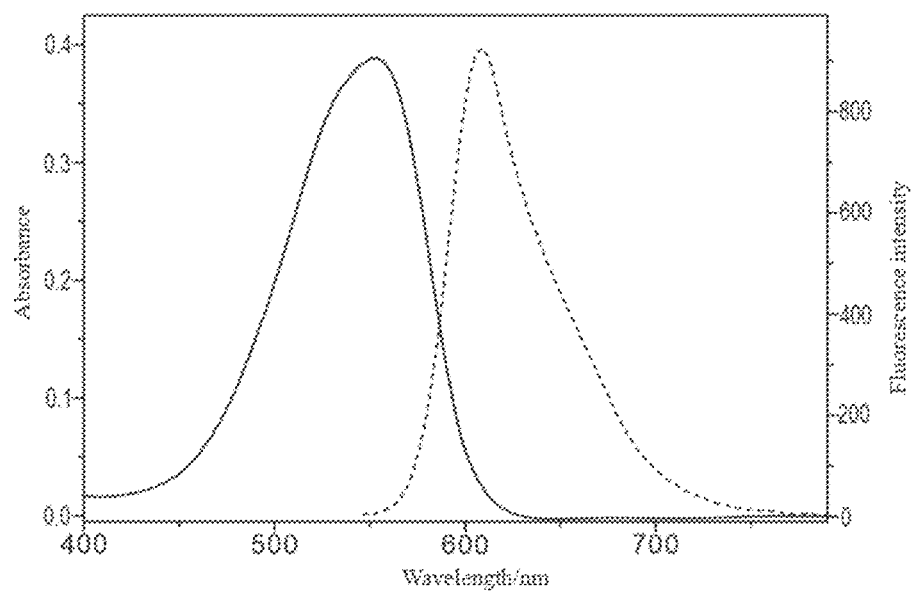
FIG. 13 shows the ultraviolet-visible absorption spectrum and fluorescence spectrum of dye 3e in chloroform.

The photo stability of dyes 2a-2e, and 3a-e (with a concentration of 10 μM) prepared above was tested. Corresponding weights of dyes 2a-2e and 3a-e and their references coumarin and Nile red were weighed, and dissolved in acetonitrile (at a concentration of 10 μM) respectively. All the samples were irradiated with a Philips iodine tungsten lamp (500 W), and the distance between the lamp and the sample was set to 25 cm. An 8 cm-thick NaNO$_2$ (60 g·L$^{-1}$) cold trap was positioned between the lamp and the sample, to eliminate heat and short-wavelength light. The irradiation was continued for 6 hrs, during which the ultraviolet fluorescence was tested every half an hour. After 6 hrs, the light stability was measured by residual absorptivity calculated based on the change in the absorption intensity at various times before and after the irradiation. As shown in FIGS. 2 and 3, after 6 hrs of continuous irradiation, the residual absorptivity of coumarin is 94%, and the residual absorptivity of Nile Red is 97%. The residual absorptivity of dyes 2a-e, and 3a-e is 2a: 93%, 2b: 92%, 2c: 95%, 2d: 91%, 2e: 97%, 3a: 93%, 3b: 92%, 3c: 94%, 3d: 93%, 3e: 92%. It can be seen that dyes 2a-2e and 3a-e have higher photo stability.

Example 4

The ultraviolet absorption and fluorescence emission of the dyes prepared above (at a concentration of 10 μM) in chloroform were tested. The horizontal ordinate is the wavelength, and the vertical ordinate is the absorbance and fluorescence intensity, respectively. The results are shown in FIGS. 4 to 13.

In the ultraviolet-visible absorption spectrum, dye 2a has the maximum absorption at 388 nm; and in the fluorescence spectrum, dye 2a has the highest fluorescence intensity at 457 nm, where the excitation wavelength is 380 nm, and the slit width is 3 nm/1.5 nm. In the ultraviolet-visible absorption spectrum, dye 2b has a maximum absorption wavelength of 386 nm; and in the fluorescence spectrum, dye 2b has a maximum emission wavelength of 459 nm, where the excitation wavelength is 385 nm, and the slit width is 3 nm/1.5 nm. In the ultraviolet-visible absorption spectrum, dye 2c has a maximum absorption wavelength of 385 nm; and in the fluorescence spectrum, dye 2c has a maximum emission wavelength of 455 nm, where the excitation wavelength is 380 nm, and the slit width is 3 nm/1.5 nm. In the ultraviolet-visible absorption spectrum, dye 2d has the maximum absorption at 380 nm; and in the fluorescence spectrum, dye 2d has the highest fluorescence intensity at 457 nm, where the excitation wavelength is 380 nm, and the slit width is 3 nm/1.5 nm. In the ultraviolet-visible absorption spectrum, dye 2e has a maximum absorption wavelength of 385 nm; and in the fluorescence spectrum, dye 2e has a maximum emission wavelength of 458 nm, where the excitation wavelength is 385 nm, and the slit width is 3 nm/1.5 nm. In the ultraviolet-visible absorption spectrum, dye 3a has the maximum absorption at 554 nm; and in the fluorescence spectrum, dye 3a has the highest fluorescence intensity at 604 nm, where the excitation wavelength is 550 nm, and the slit width is 1.5 nm/3 nm. In the ultraviolet-visible absorption spectrum, dye 3b has a maximum absorption wavelength of 552 nm; and in the fluorescence spectrum, dye 3b has a maximum emission wavelength of 597 nm, where the excitation wavelength is 550 nm, and the slit width is 1.5 nm/3 nm. In the ultraviolet-visible absorption spectrum, dye 3c has a maximum absorption wavelength of 552 nm; and in the fluorescence spectrum, dye 3c has a maximum emission wavelength of 621 nm, where the excitation wavelength is 550 nm, and the slit width is 1.5 nm/3 nm. In the ultraviolet-visible absorption spectrum, dye 3d has a maximum absorption wavelength of 551 nm; and in the fluorescence spectrum, dye 3d has a maximum emission wavelength of 607 nm, where the excitation wavelength is 545 nm, and the slit width is 1.5 nm/3 nm. In the ultraviolet-visible absorption spectrum, dye 3e has a maximum absorption wavelength of 553 nm; and in the fluorescence spectrum, dye 3e has a maximum emission wavelength of 585 nm, where the excitation wavelength is 550 nm, and the slit width is 1.5 nm/3 nm. The above UV absorption and fluorescence emission test methods are conventional methods.

Example 5

Figure 14:
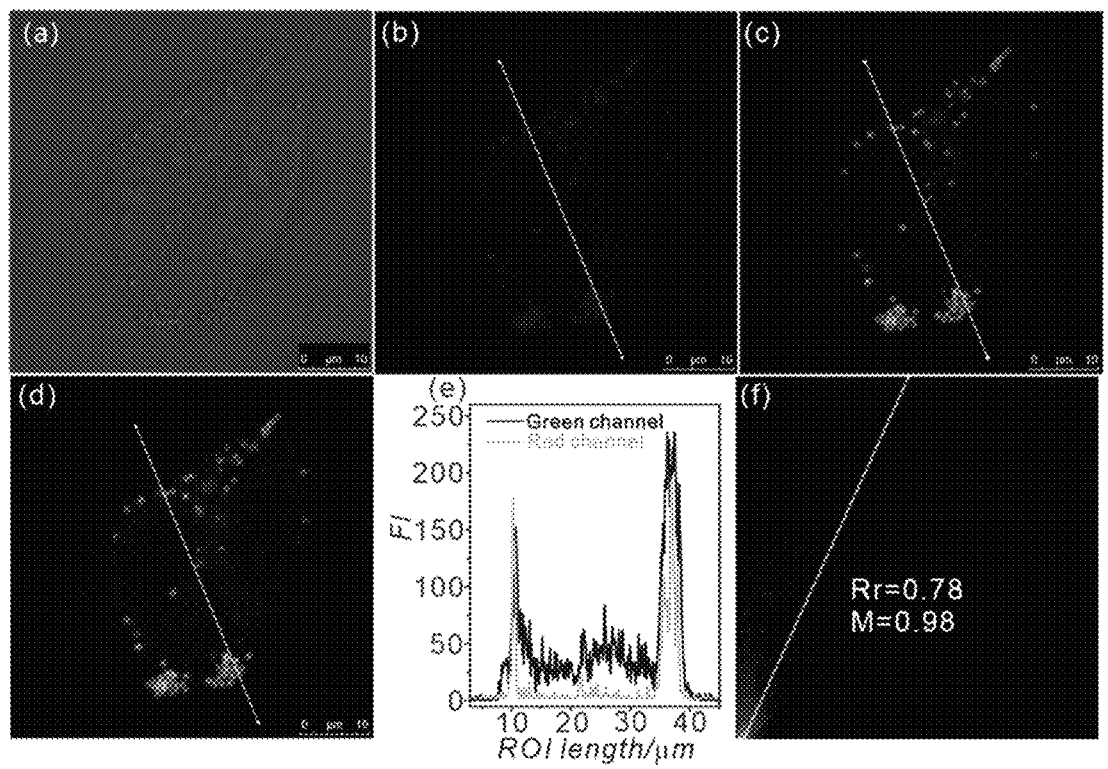
FIG. 14 is a cell image with Compound 2 in HeLa cells.
Figure 20:
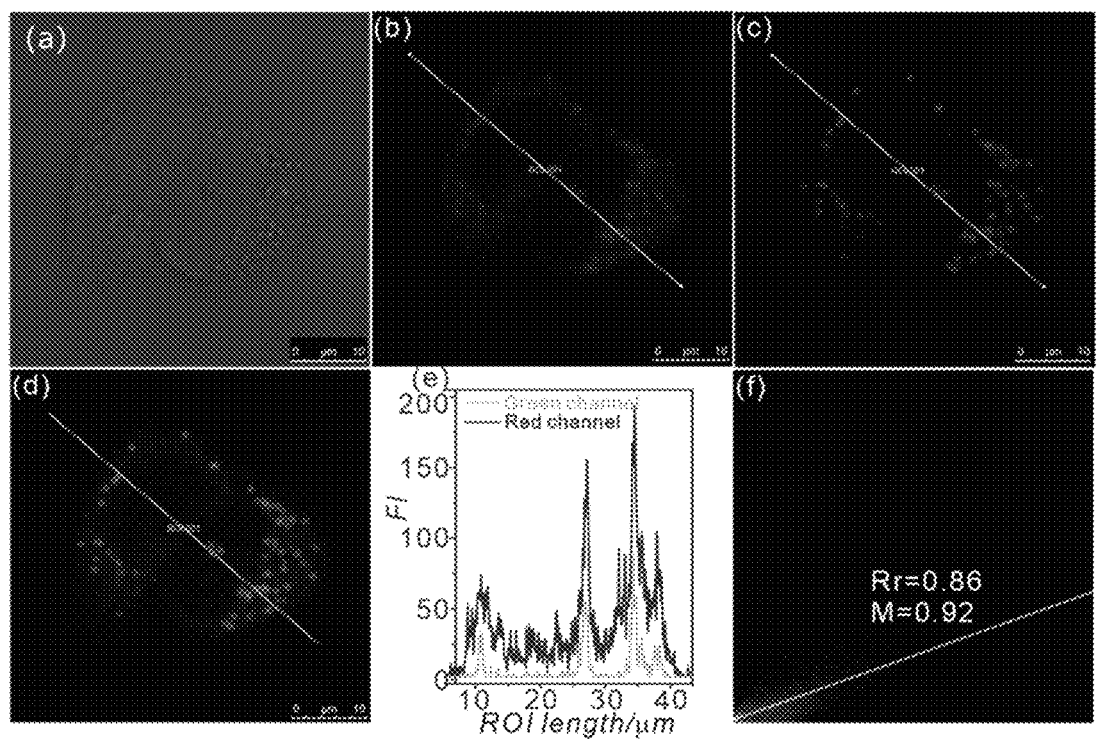
FIG. 20 is a cell image with Compound 3 in HeLa cells.

To test the fluorescent labeling ability of Compounds 2 and 3 before being chemically bonded to an amide derivative, Compound 2 or Compound 3 was prepared into a mother liquor in DMSO (dimethyl sulfoxide), and then added to a conventional cell culture medium to give a concentration of Compound 2 or Compound 3 in the cell culture medium of 2 μM. HeLa cells were co-cultured for 10 min in an incubator at saturated humidity, 37° C., and 5% $CO_2$ (the experiment was same below), then washed three times with a PBS buffer, and imaged under a laser confocal microscope. In the blue channel, light of 405 nm was used for excitation, and a fluorescence signal in the range of 410-500 nm was collected; in the green channel, light of 488 nm was used for excitation, and a fluorescence signal in the range of 500-550 nm was collected; and in the red channel, light of 561 nm was used for excitation, and a fluorescence signal in the range of 570-750 nm was collected. The results show that lipid droplets in HeLa cells were stained with Compound 2. The results are shown in FIG. 14, where (a) is the bright-field image, (b) is the cell image with dye 2, (c) is the cell image of lipid droplets with a green marker, (d) is an overlapped image with blue channel and green channel, (e) shows the fluorescence intensity of the ROI line in the overlapped image, and (f) shows a colocalization assay, with a colocalization coefficient of 0.78. Compound 3 also has lipid droplet labeling ability in HeLa cells, and the results are shown in FIG. 20, where (a) is the bright-field image, (b) is the cell image with Compound 3, (c) is the cell image of lipid droplets with a green marker, (d) is an overlapped image with red channel and green channel, (e) shows the fluorescence intensity of the ROI line in the overlapped image, and (f) shows a colocalization assay, with a colocalization coefficient of 0.86

Figure 15:
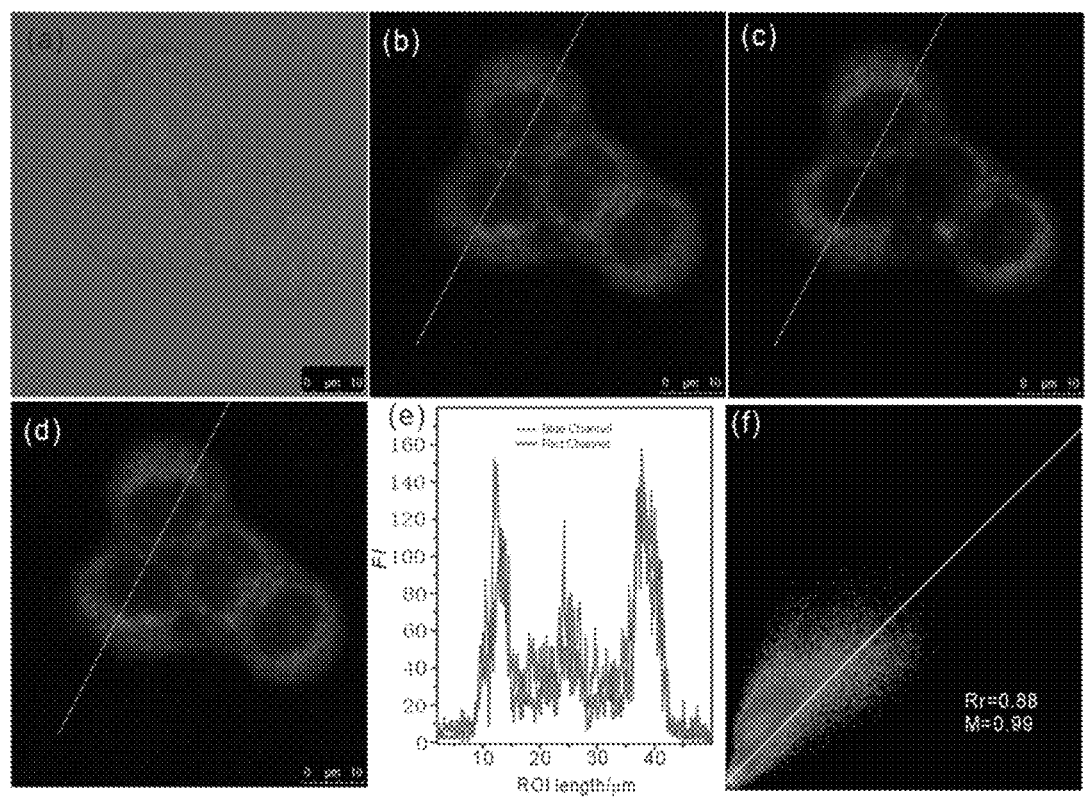
FIG. 15 is a cell image with dye 2a in HeLa cells.

To test the fluorescent labeling ability of Compound 2a compared with commercial mitochondrial markers, dye 2a was formulated into a mother liquor in DMSO (dimethyl sulfoxide), and then added to a conventional cell culture medium to give a concentration of dye 2a in the cell culture medium of 2 μM. HeLa cells were co-cultured for 10 min in an incubator at saturated humidity, 37° C., and 5% $CO_2$ (the experiment was same below). The red mitochondrial marker Mito Tracker© Red CMXRos (100 nm) was added, and the cells were co-incubated for another 10 min, washed three times with a PBS buffer, and imaged under a laser confocal microscope. In the blue channel, light of 405 nm was used for excitation, and a fluorescence signal in the range of 410-500 nm was collected; and in the red channel, light of 561 nm was used for excitation, and a fluorescence signal in the range of 570-750 nm was collected. The results are shown in FIG. 15, where (a) is the bright-field image, (b) is the cell image with dye 2a, (c) is the cell image with the red mitochondrial marker, (d) is an overlapped image with blue channel and red channel, (e) shows the fluorescence intensity of the ROI line in the overlapped image, and (f) shows a colocalization assay, with a colocalization coefficient of 0.88. The results show that the fluorescence image with dye 2a in mitochondria is consistent with the fluorescence image with the commercial red mitochondrial marker Mito Tracker© Red CMXRos, and the intensity is comparable, indicating that dye 2a has mitochondria labeling ability in HeLa cells, and can be used as a blue mitochondrial marker.

Figure 16:
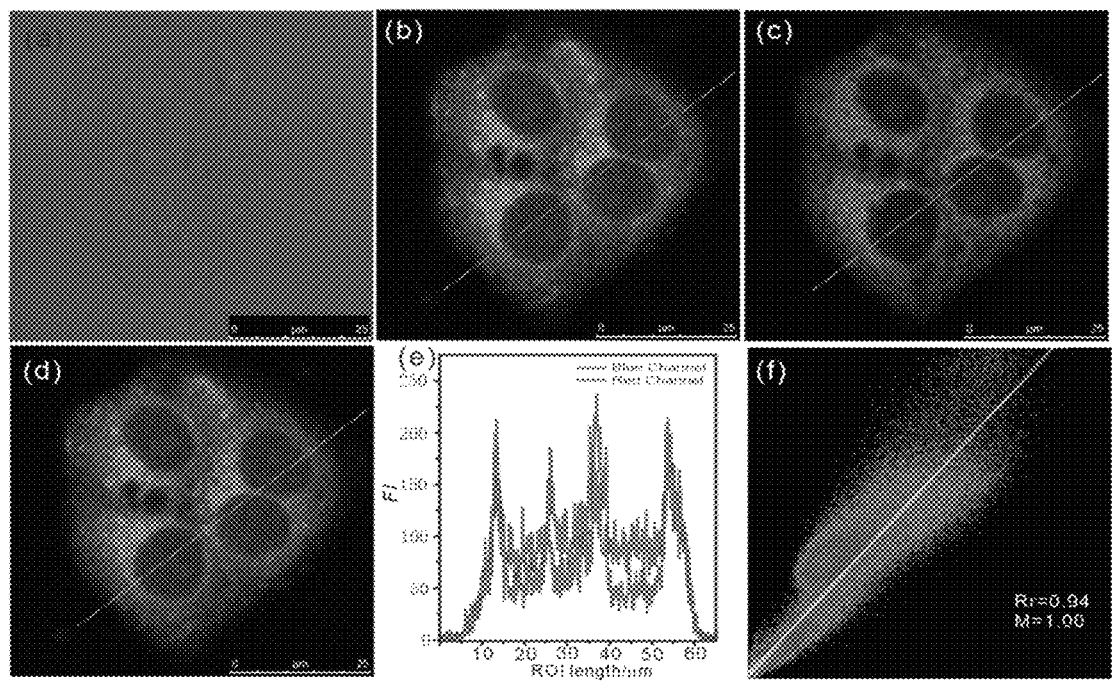
FIG. 16 is a cell image with dye 2b in HeLa cells.
Figure 17:
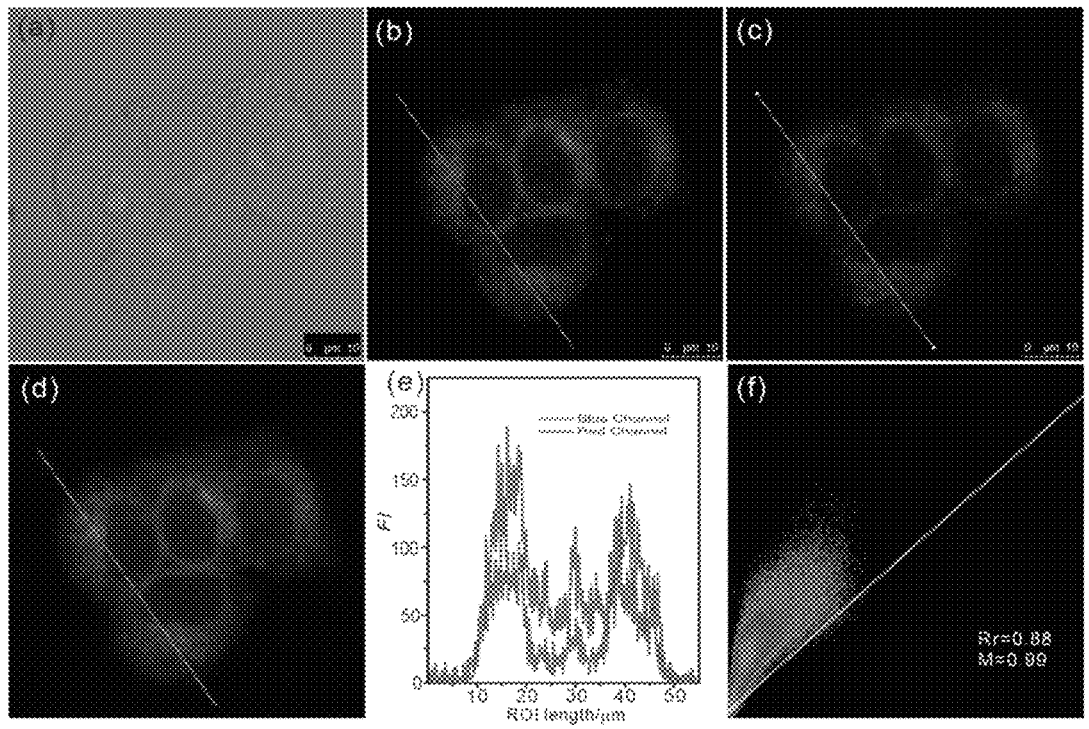
FIG. 17 is a cell image with dye 2c in HeLa cells.
Figure 18:
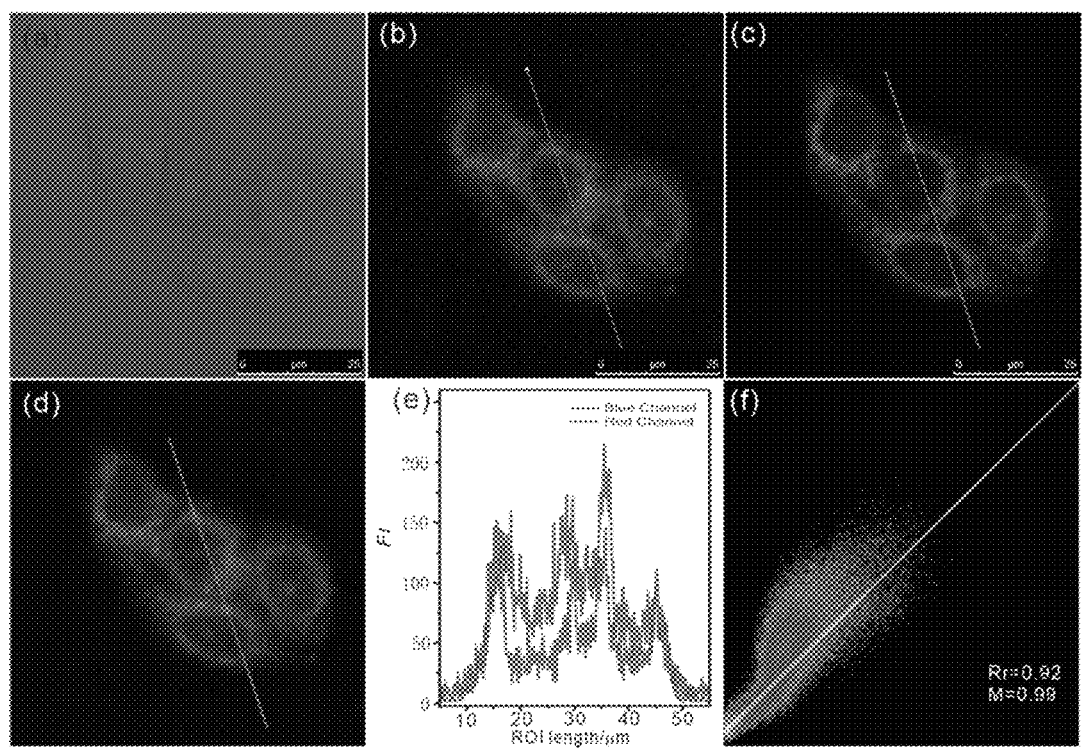
FIG. 18 is a cell image with dye 2d in HeLa cells.
Figure 19:
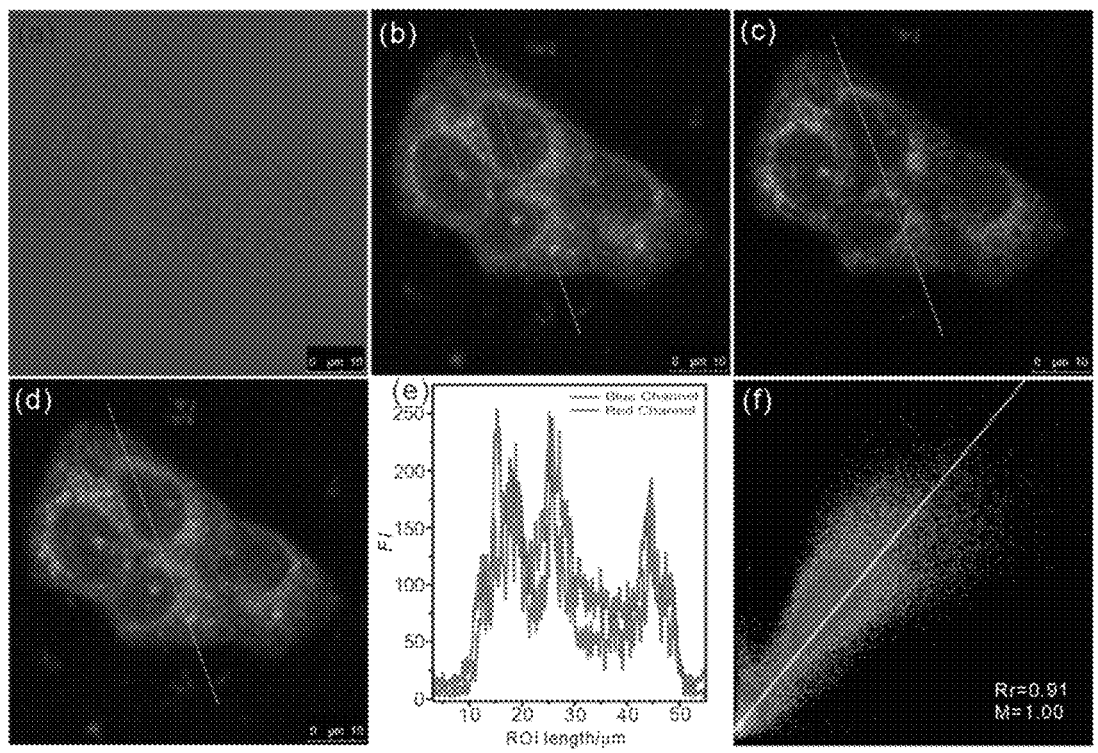
FIG. 19 is a cell image with dye 2e in HeLa cells.

The experiment method with dye 2b (2 μM), dye 2c (2 μM), dye 2d (2 μM), and dye 2e (2 μM) was the same with that with dye 2a, except that dye 2a was replaced. The results are shown in FIG. 16, where (a) is the bright-field image, (b) is the cell image with dye 2b, (c) is the cell image with red mitochondrial marker, (d) is an overlapped image with blue channel and red channel, (e) shows the fluorescence intensity of the ROI line in the overlapped image, and (f) shows a colocalization assay, with a colocalization coefficient of 0.94. The results are shown in FIG. 17, where (a) is the bright-field image, (b) is the cell image with dye 2c, (c) is the cell image with red mitochondrial marker, (d) is an overlapped image with blue channel and red channel, (e) shows the fluorescence intensity of the ROI line in the overlapped image, and (f) shows a colocalization assay, with a colocalization coefficient of 0.88. The results are shown in FIG. 18, where (a) is the bright-field image, (b) is the cell image with dye 2d, (c) is the cell image with red mitochondrial marker, (d) is an overlapped image with blue channel and red channel, (e) shows the fluorescence intensity of the ROI line in the overlapped image, and (f) shows a colocalization assay, with a colocalization coefficient of 0.92. The results are shown in FIG. 19, where (a) is the bright-field image, (b) is the cell image with dye 2e, (c) is the cell image with red mitochondrial marker, (d) is an overlapped image with blue channel and red channel, (e) shows the fluorescence intensity of the ROI line in the overlapped image, and (f) shows a colocalization assay, with a colocalization coefficient of 0.91. The results show that the fluorescence image with dyes 2b-e in mitochondria is consistent with the fluorescence image with the commercial red mitochondrial marker Mito Tracker© Red CMXRos, and the intensity is comparable, indicating that dye 2b, dye 2c, dye 2d, and dye 2e have mitochondria labeling ability in HeLa cells, and can be used as a blue mitochondrial marker.

Figure 21:
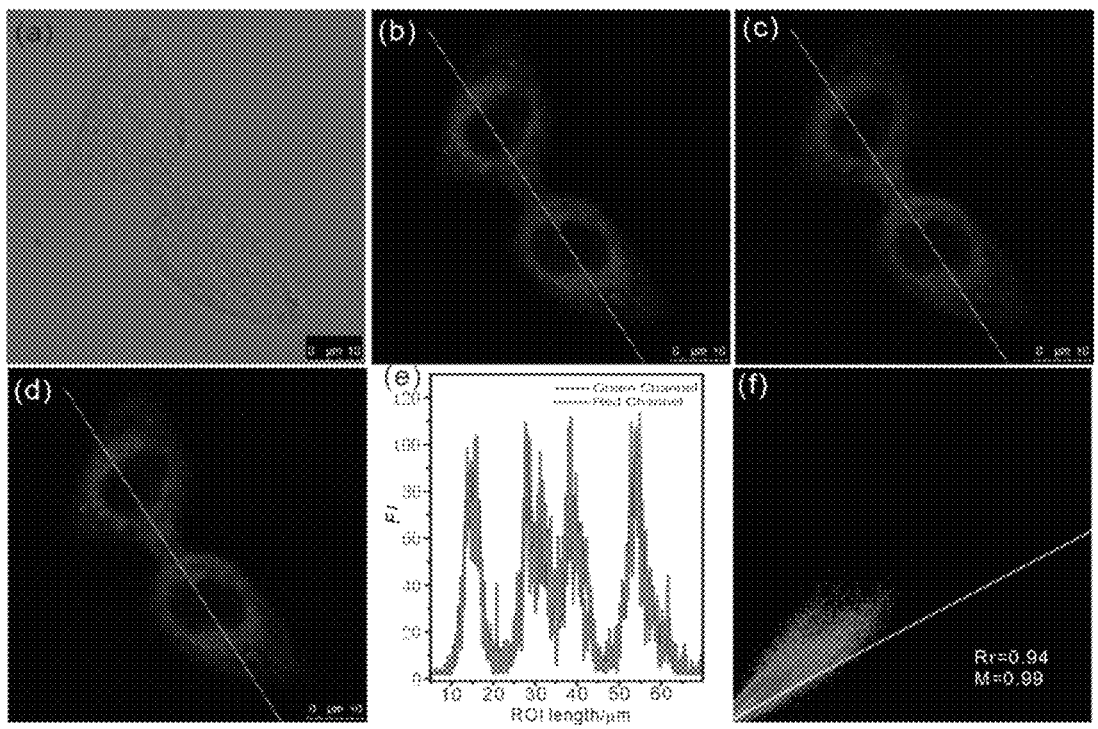
FIG. 21 is a cell image with dye 3a in HeLa cells.

Dye 3a was formulated into a mother liquor in DMSO (dimethyl sulfoxide), and then added to a conventional cell culture medium to give a concentration of dye 3a in the cell culture medium of 2 μM. HeLa cells were co-cultured for 10 min in an incubator at saturated humidity, 37° C., and 5% $CO_2$ (the experiment was same below). The green mitochondrial marker Mito Tracker® Green FM (100 nm) was added, and the cells were co-incubated for another 10 min, washed three times with a PBS buffer, and imaged under a laser confocal microscope. In the red channel, light of 561 nm was used for excitation, and a fluorescence signal in the range of 570-750 nm was collected. In the green channel, light of 488 nm was used for excitation, and a fluorescence signal in the range of 500-550 nm was collected. The results are shown in FIG. 21, where (a) is the bright-field image, (b) is the cell image with dye 3a, (c) is the cell image with the green mitochondrial marker, (d) is an overlapped image with red channel and green channel, (e) shows the fluorescence intensity of the ROI line in the overlapped image, and (f) shows a colocalization assay, with a colocalization coefficient of 0.94. The results show that the fluorescence image with dye 3a in mitochondria is consistent with the fluorescence image of the commercial green mitochondrial marker Mito Tracker© Green FM, and the intensity is comparable, indicating that dye 3a has mitochondria labeling ability in HeLa cells, and can be used as a red mitochondrial marker.

Figure 22:
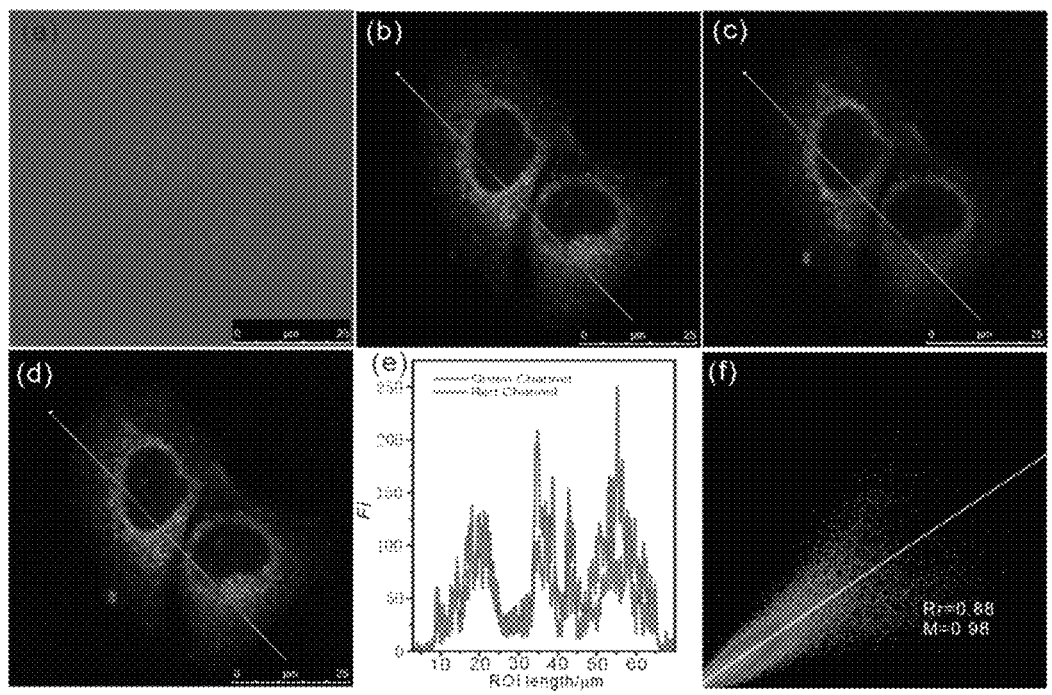
FIG. 22 is a cell image with dye 3b in HeLa cells.
Figure 23:
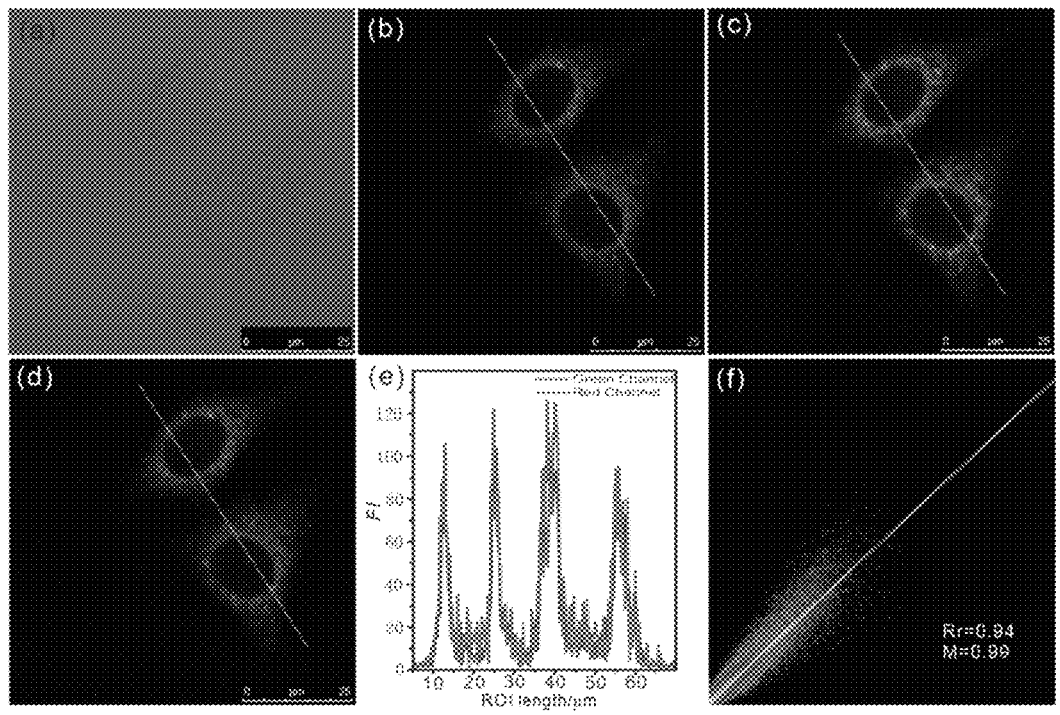
FIG. 23 is a cell image with dye 3c in HeLa cells.
Figure 24:
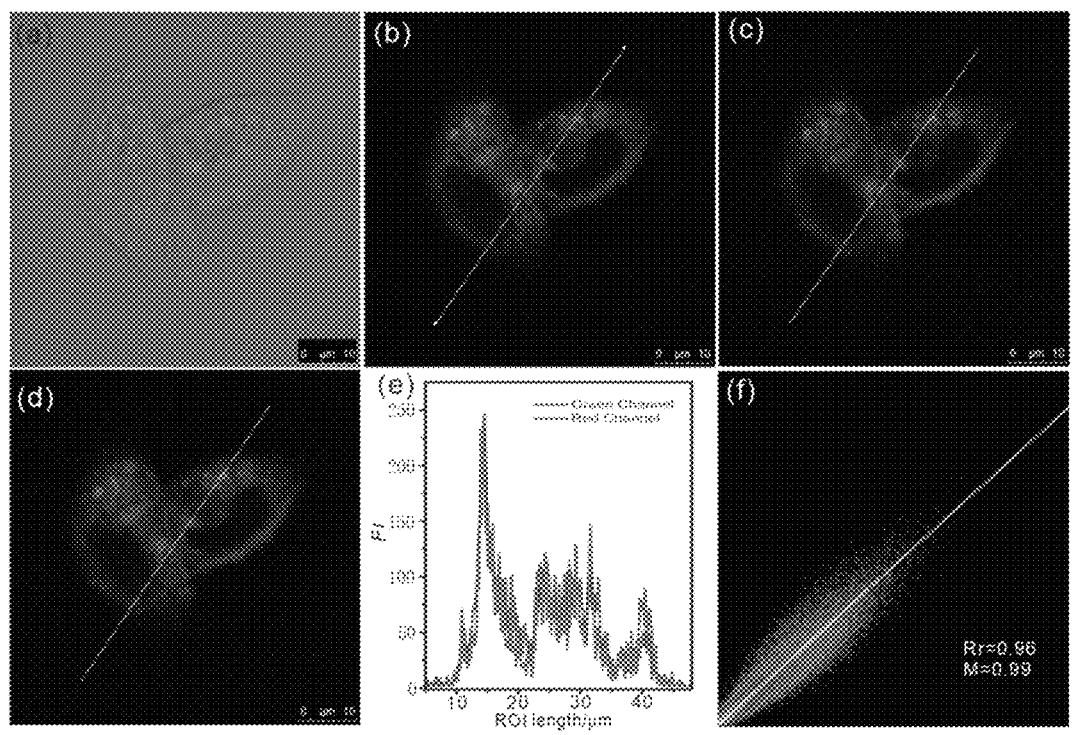
FIG. 24 is a cell image with dye 3d in HeLa cells.
Figure 25:
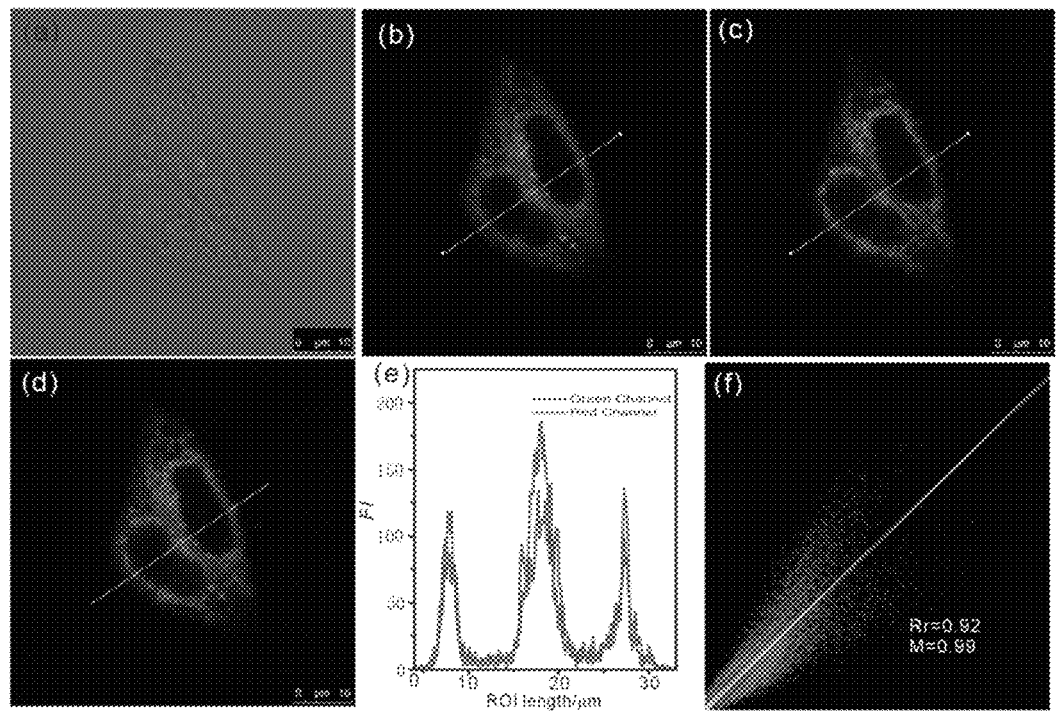
FIG. 25 is a cell image with dye 3e in HeLa cells.

The experiment method with dye 3b (2 µM), dye 3c (2 µM), dye 3d (2 µM), and dye 3e (2 µM) was the same with that with dye 3a, except that dye 3a was replaced. The results are shown in FIG. 22, where (a) is the bright-field image, (b) is the cell image with dye 3b, (c) is the cell image with the green mitochondrial marker, (d) is an overlapped image with red channel and green channel, (e) shows the fluorescence intensity of the ROI line in the overlapped image, and (f) shows a colocalization assay, with a colocalization coefficient of 0.88. The results are shown in FIG. 23, where (a) is the bright-field image, (b) is the cell image with dye 3c, (c) is the cell image with the green mitochondrial marker, (d) is an overlapped image with red channel and green channel, (e) shows the fluorescence intensity of the ROI line in the overlapped image, and (f) shows a colocalization assay, with a colocalization coefficient of 0.94. The results are shown in FIG. 24, where (a) is the bright-field image, (b) is the cell image with dye 3d, (c) is the cell image with the green mitochondrial marker, (d) is an overlapped image with red channel and green channel, (e) shows the fluorescence intensity of the ROI line in the overlapped image, and (f) shows a colocalization assay, with a colocalization coefficient of 0.96. The results are shown in FIG. 25, where (a) is the bright-field image, (b) is the cell image with dye 3e, (c) is the cell image with the green mitochondrial marker, (d) is an overlapped image with red channel and green channel, (e) shows the fluorescence intensity of the ROI line in the overlapped image, and (f) shows a colocalization assay, with a colocalization coefficient of 0.92. The results show that the fluorescence image of dyes 3b-e in mitochondria is consistent with the fluorescence image of the commercial green mitochondrial marker Mito Tracker® Green FM, and the intensity is comparable, indicating that dye 3b, dye 3c, dye 3d, and dye 3e has mitochondria labeling ability in HeLa cells, and can be used as a red mitochondrial marker.

Example 6

In addition, the cytotoxicity of dyes 2a-e or 3a-e was also tested in the present invention. The viability of HeLa cells in the presence of these dyes was measured by the CCK-8 method. The HeLa cells were incubated with different concentrations of dyes (2, 4, 6, 8 and 10 µM) for 6 hrs. FIG. 26a shows the cytotoxicity test results of dyes 2a-e, and FIG. 26b shows the cytotoxicity test results of dyes 3a-e. The results show that they have good cell viability and are suitable for live cell imaging. Moreover, the survival rate of HeLa cells after 6 hrs of incubation with dyes 3a-c is over 100%, which indicates that dyes 3a-c is non-toxic, and can promote cell growth.

Figure 26:
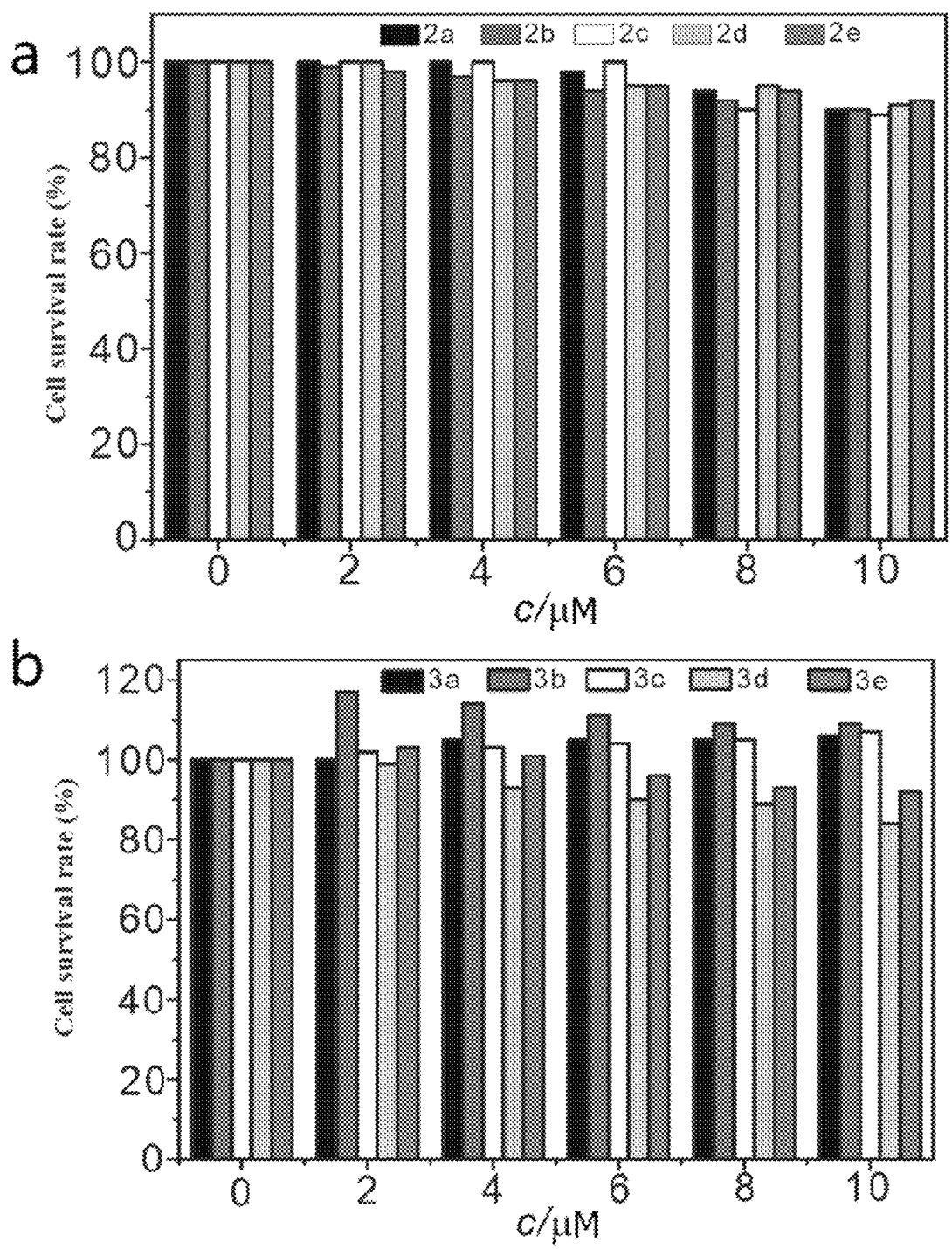
FIG. 26 shows the cytotoxicity test results of dyes 2a-e and 3a-e.

In FIG. 26, cell survival rate (%)=$(A_{sample}-A_b)/(A_c-A_b)$, where $A_c$ is the negative control (including culture medium and cells, without test dye), $A_b$: blank (including test dye and culture medium, without cells), and $A_{sample}$: test group (including culture medium, cells and dye to be tested).

Example 7

Figure 27:
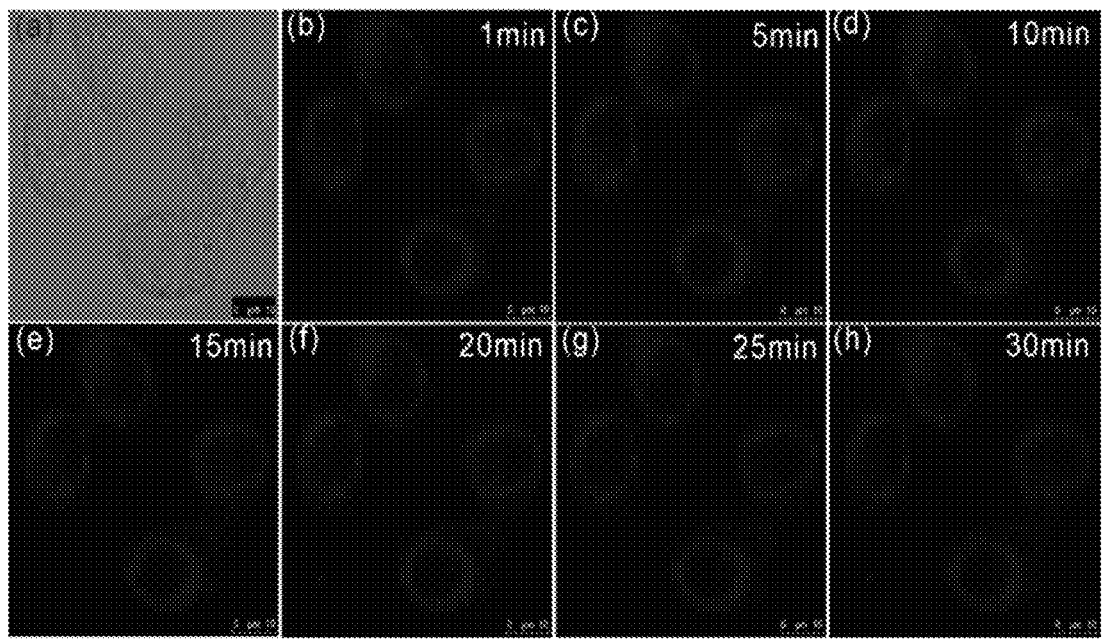
Figure 28:
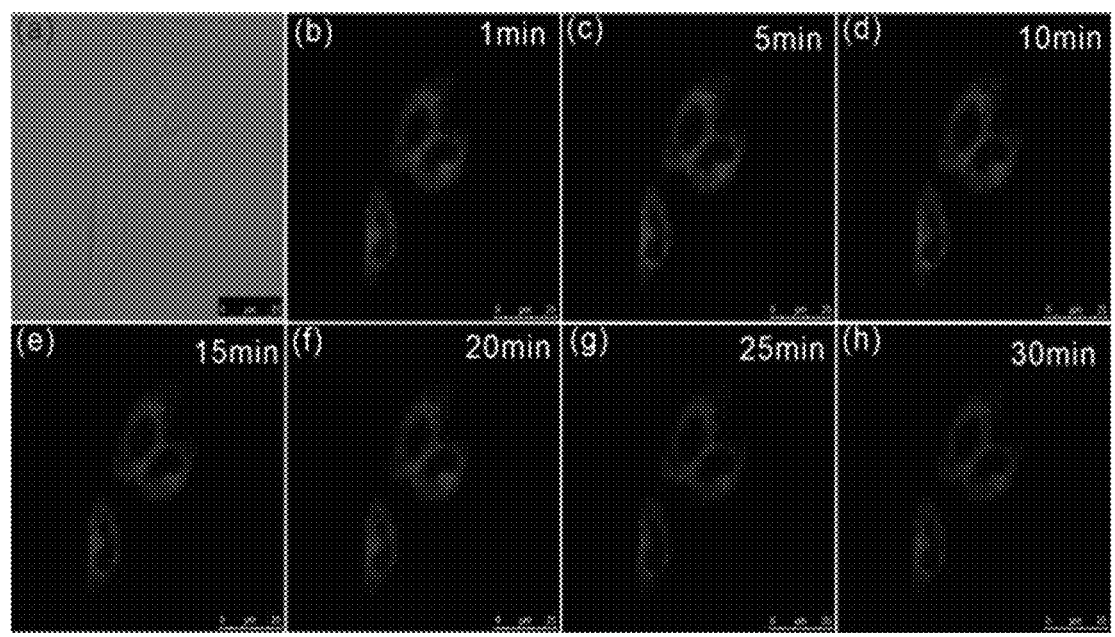

As we all know, as a biomarker, it is very important to have excellent resistance to photobleaching. Therefore, the dyes 2a (5 µM) and 3a (5 µM) were selected for photobleaching studies in living cells. In FIG. 27, FIG. 27(a) is a bright-field image; and FIGS. 27(b-h) show the fluorescence images of HeLa cells containing dye 2a after continuous irradiation with a laser source (561 nm) for 1, 5, 10, 15, 20, 25, and 30 min. In FIG. 28, FIG. 28(a) is a bright-field image; and FIGS. 28(b-h) show the fluorescence images of HeLa cells containing dye 3a after continuous irradiation with a laser source (405 nm) for 1, 5, 10, 15, 20, 25, and 30 min. The results show that after 1, 5, 10, 15, 20, 25, and 30 min of continuous irradiation, dyes 2a and 3a still have the mitochondria imaging ability, with only a slight decrease in fluorescence intensity.

It can be seen that the present invention provides a neutral fluorescent mitochondrial marker as an amide derivative for the first time, which enables imaging of mitochondria in the cells after co-incubation with cells. In the present invention, the organelle targeting ability of a dye is regulated by creative modification of its structure while the optical performance of the dye is improved. The dye has low cytotoxicity during cell imaging, has little damage to biological samples, and is not affected by other organelles. By using the dye, the cell sample can be observed for a long time, and there is no need to permeate the cells or immobilize the cells. The cells can be monitored in real time without being affected by other organelles. The experimental results show that the dye of the present invention has excellent mitochondria targeting performance.

While preferred embodiments of the present invention have been described above, the present invention is not limited thereto. It should be appreciated that some improvements and variations can be made by those skilled in the art without departing from the technical principles of the present invention, which are also contemplated to be within the scope of the present invention.

What is claimed is:

1. A neutral fluorescent mitochondrial marker as an amide derivative, represented by one of Formulas (I)-(IV):

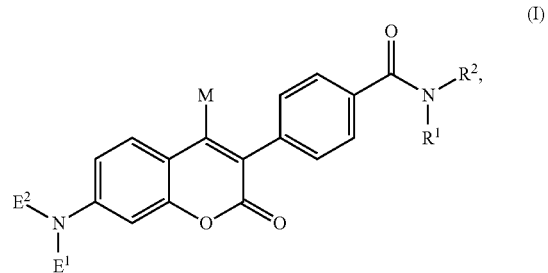

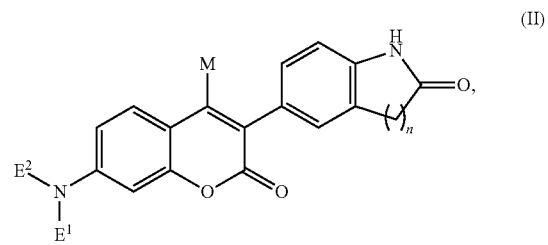

-continued

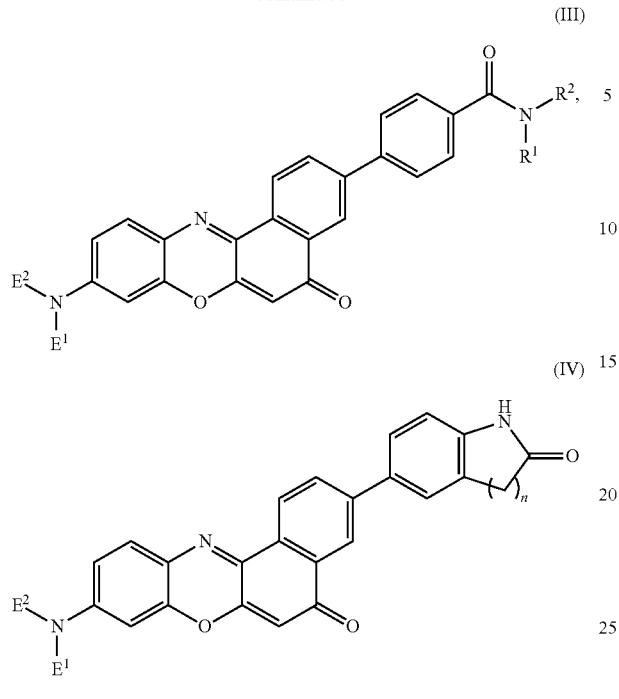

wherein $R^1$ and $R^2$ are each independently selected from hydrogen or an alkyl group having 1 to 6 carbon atoms; M, $E^1$, and $E^2$ are each independently selected from an alkyl group having 1 to 6 carbon atoms; and n is any integer from 1 to 3.

2. The neutral fluorescent mitochondrial marker as an amide derivative according to claim 1, wherein $R^1$ and $R^2$ are each independently selected from hydrogen or methyl; M is methyl; $E^1$ and $E^2$ are both ethyl; and n is 1 or 2.

3. A method for preparing a neutral fluorescent mitochondrial marker as an amide derivative according to claim 1, comprising steps of:

reacting a compound of Formula (2) with a compound of Formulas (1a-c) or Formulas (1d-e) in an organic solvent under a weakly basic condition, to obtain a neutral fluorescent mitochondrial marker as an amide derivative of Formula (I) or Formula (II); or reacting a compound of Formula (3) with a compound of Formulas (1a-c) or Formulas (1d-e) in an organic solvent under a weakly basic condition, to obtain a neutral fluorescent mitochondrial marker as an amide derivative of Formula (III) or Formula (IV), wherein the structural formulas of Formulas (1a-c), (1d-e), (2) and (3) are shown below:

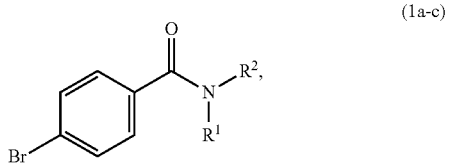

4. The method according to claim 3, wherein the reactions are all carried out in the presence of a noble metal salt catalyst.

5. The method according to claim 4, wherein the noble metal salt catalyst comprises a palladium salt catalyst.

6. The method according to claim 3, wherein the reactions are carried at 85-110° C.

7. A fluorescent mitochondrial labeling reagent, comprising:
the neutral fluorescent mitochondrial marker according to claim 1.

8. The fluorescent mitochondrial labeling reagent according to claim 7, wherein the fluorescent mitochondrial labeling reagent targets mitochondria in cancer cells.

9. The fluorescent mitochondrial labeling reagent according to claim 7, further comprising a method for cell imaging using the fluorescent mitochondrial labeling reagent, which comprises steps of:
co-incubating the fluorescent mitochondrial labeling reagent and cells for 10 min or more at 37° C. and 5% $CO_2$, then imaging the cells under a laser confocal microscope, and collecting a fluorescent signal.

10. The fluorescent mitochondrial labeling reagent according to claim 9, wherein when the fluorescent mitochondrial labeling reagent comprises the neutral fluorescent mitochondrial marker as an amide derivative represented by Formula (I) or Formula (II), the reagent is excited using a 405 nm light source, and a fluorescent signal in the range of 410 to 500 nm is collected; and
when the fluorescent mitochondrial labeling reagent comprises the neutral fluorescent mitochondrial marker as an amide derivative represented by Formula (III) or Formula (IV) the reagent is excited using a 561 nm light source, and a fluorescent signal in the range of 570 to 750 nm is collected.

* * * * *